(12) United States Patent
Chegani et al.

(10) Patent No.: US 11,717,177 B2
(45) Date of Patent: Aug. 8, 2023

(54) BLOOD PRESSURE MEASUREMENT

(71) Applicant: BEIJING SHUNYUAN KAIHUA TECHNOLOGY LIMITED, Beijing (CN)

(72) Inventors: Rana Sadeghi Chegani, Coquitlam (CA); Yan Vule, Port Moody (CA); Kongqiao Wang, Anhui (CN); Artem Galeev, Vancouver (CA); Yoav Aminov, Tel Aviv (IL)

(73) Assignee: BELING SHUNYUAN KAIHUA TECHNOLOGY LIMITED, Beijing (CN)

( * ) Notice: Subject to any disclaimer, the term of this patent is extended or adjusted under 35 U.S.C. 154(b) by 491 days.

(21) Appl. No.: 16/875,135

(22) Filed: May 15, 2020

(65) Prior Publication Data

US 2021/0353164 A1    Nov. 18, 2021

(51) Int. Cl.
| | |
|---|---|
| *G06F 11/30* | (2006.01) |
| *A61B 5/021* | (2006.01) |
| *A61B 5/00* | (2006.01) |
| *G06N 20/00* | (2019.01) |
| *A61B 5/0285* | (2006.01) |

(52) U.S. Cl.
CPC ........ *A61B 5/02125* (2013.01); *A61B 5/0285* (2013.01); *A61B 5/681* (2013.01); *A61B 5/7221* (2013.01); *A61B 5/7267* (2013.01); *G06N 20/00* (2019.01)

(58) Field of Classification Search
CPC .................................................. A61B 5/02125
See application file for complete search history.

(56) References Cited

U.S. PATENT DOCUMENTS

2019/0246982 A1*   8/2019  Mackellar ............. A61M 21/00
2021/0353165 A1*  11/2021  Galeev ............... A61B 5/02125

* cited by examiner

*Primary Examiner* — Phuong Huynh
(74) *Attorney, Agent, or Firm* — Young Basile Hanlon & MacFarlane, P.C.

(57) ABSTRACT

A method includes obtaining a baseline blood pressure at an initial time window; estimating a plurality of intermediate blood pressure change estimates, the intermediate blood pressure change estimates correspond to respective time windows that are subsequent to the initial time window; estimating a final blood pressure change estimate between the initial and final time windows; and obtaining the blood pressure by adding the baseline blood pressure to the final blood pressure change estimate. Estimating the final blood pressure includes estimating a first blood pressure change between the initial time window and the final time window; estimating a plurality of second blood pressure changes, each second blood pressure change is between a respective time window of the respective time windows and the final time window; and estimating the final blood pressure change estimate as a combination of the first blood pressure change and the plurality of second blood pressure changes.

19 Claims, 16 Drawing Sheets

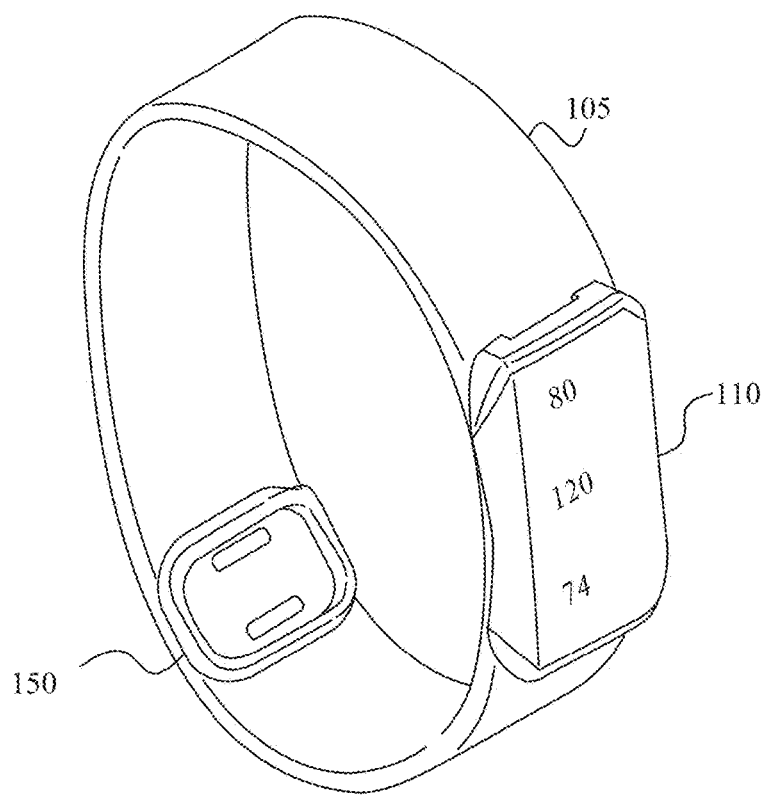
FIG. 5A
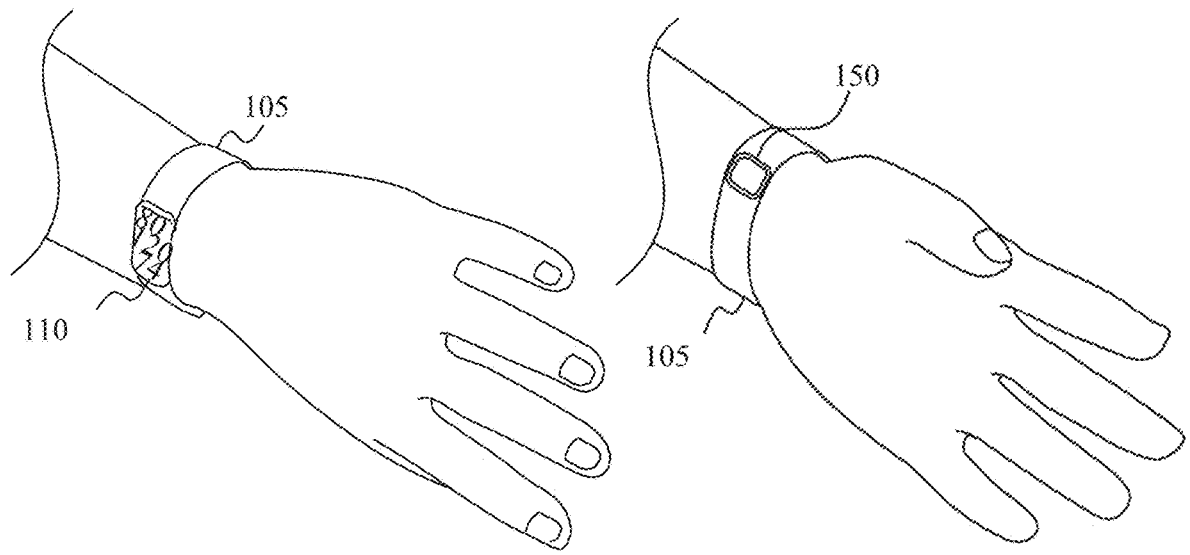
FIG. 5B FIG. 5C

BLOOD PRESSURE MEASUREMENT

CROSS REFERENCES TO RELATED APPLICATION(S)

None.

TECHNICAL FIELD

This disclosure relates generally to detecting physiological information of a user through a number of sensors of a wearable device, and more specifically to detecting blood pressure using, mainly, pressure sensors.

BACKGROUND

Many portable devices have been developed in which sensors are used to detect variation in blood flow through arteries or blood volume in subcutaneous tissue. Applications include the monitoring of heart rate, glucose level, apnea, respiratory stress, and other physiological conditions.

High blood pressure is a major risk for heart disease. By some estimates, high blood pressure affects one in every three adults in the United States. By some other estimates, in developing and developed countries, respectively, 45% and 55% of high-blood-pressure sufferers are not aware of their condition.

The ability to monitor blood pressure via a portable (e.g., wearable) device is desirable.

SUMMARY

Disclosed herein are implementations of a wearable device for measuring blood pressure.

A first aspect is a method for estimating a blood pressure of a user. The method includes obtaining a baseline blood pressure at an initial time window; estimating a plurality of intermediate blood pressure change estimates, wherein the intermediate blood pressure change estimates correspond to respective time windows that are subsequent to the initial time window; estimating a final blood pressure change estimate between the initial time window and a final time window; and obtaining the blood pressure of the user by adding the baseline blood pressure to the final blood pressure change estimate. Estimating the final blood pressure includes estimating a first blood pressure change between the initial time window and the final time window; estimating a plurality of second blood pressure changes, wherein each second blood pressure change is between a respective time window of the respective time windows and the final time window; and estimating the final blood pressure change estimate as a combination of the first blood pressure change and the plurality of second blood pressure changes.

A second aspect is an apparatus for estimating a blood pressure of a user. The apparatus includes a memory and a processor. The processor is configured to execute instructions stored in the memory to obtain, at a first time point, first features; obtain respective intermediate features at intermediate time points subsequent to the first time point; obtain final features at a final time point subsequent to the intermediate time points; obtain feature differences from the first features, at least some of the respective intermediate features, and the final features; obtain, for the feature differences, respective blood pressure difference estimates; select, from the respective blood pressure difference estimates, a first subset of first blood pressure difference estimates that form a first path from the first time point to the final time point; and combine, to obtain a first blood pressure difference between the first time point and the final time point, the first blood pressure difference estimates of the first subset of the blood pressure difference estimates.

A third aspect is a non-transitory computer-readable storage medium that includes executable instructions that, when executed by a processor, facilitate performance of operations for predicting a final current value at a final time point in situations of imbalanced training data in machine learning. The operations include obtaining, at an initial time point, initial predictive features; obtaining, at the initial time point, an initial measured value; obtaining intermediate predictive features at points between the initial time point and the final time point; obtaining, at the final time point, final predictive features; selecting a first path, where the first path corresponds to a set of first data hops from the initial time point to the final time point, where each first data hop includes starting predictive features and ending predictive features, where the starting predictive features is one of the initial predictive features or one of the intermediate predictive features, and where the ending predictive features is another of the intermediate predictive features or the final predictive features; calculating first respective predictive feature differences for the first data hops; obtaining, using the first respective predictive feature differences as inputs to a machine learning model, first respective predicted values; and combining at least the first respective predicted values to obtain the final current value.

It will be appreciated that aspects can be implemented in any convenient form. For example, aspects may be implemented by appropriate computer programs which may be carried on appropriate carrier media which may be tangible carrier media (e.g. disks) or intangible carrier media (e.g. communications signals). Aspects may also be implemented using suitable apparatus which may take the form of programmable computers running computer programs arranged to implement the methods. Aspects can be combined such that features described in the context of one aspect may be implemented in another aspect.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIGS. 5A-5C depict some aspects of an illustrative implementation of an apparatus as described herein.

DETAILED DESCRIPTION

Figure 1:
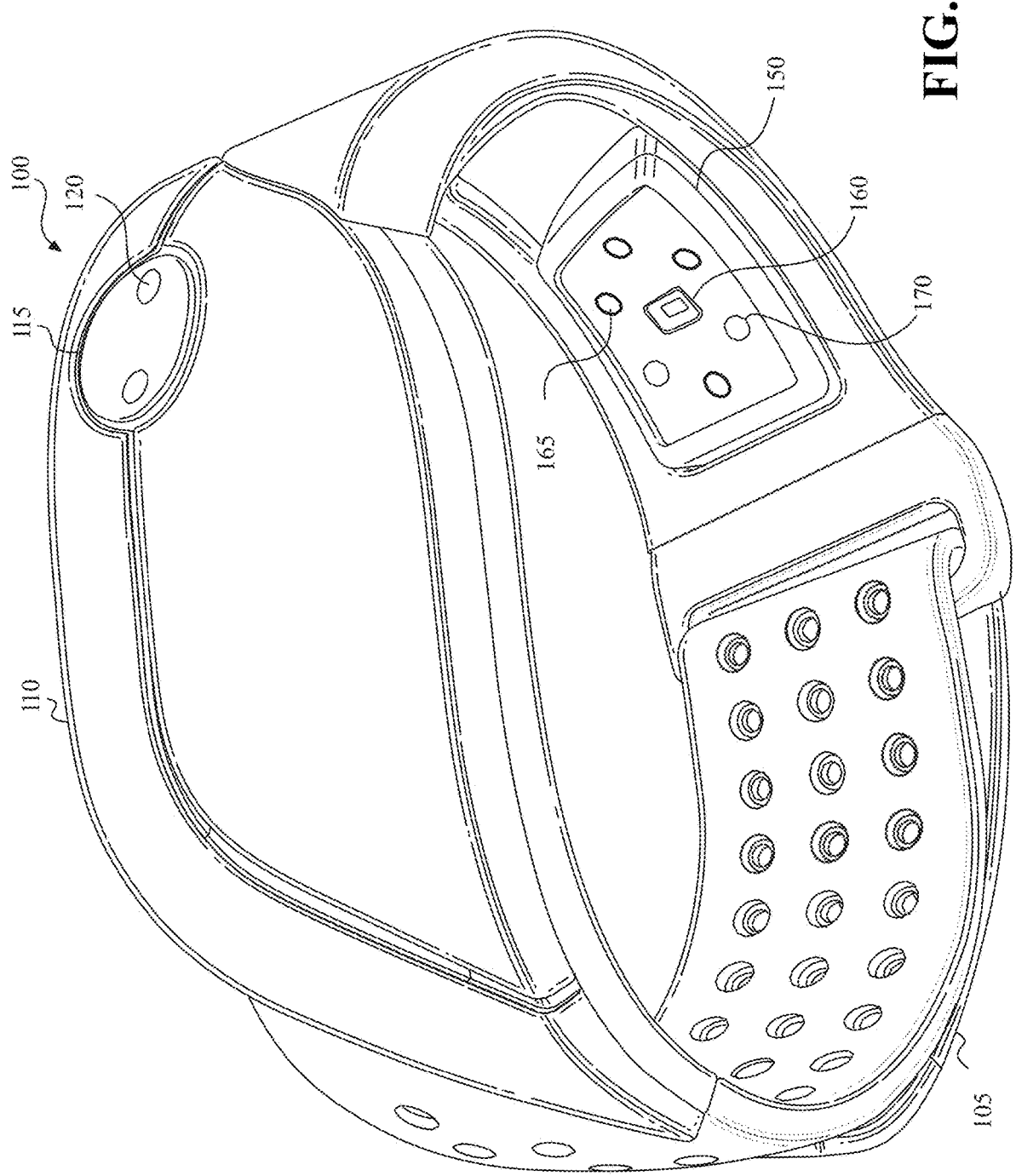
FIG. 1 depicts some aspects of an illustrative implementation of an apparatus as described herein.

Disclosed herein are implementations of an apparatus for sensing, measuring, analyzing, and displaying physiological information. In one aspect, the apparatus may be a wearable device comprising an upper module and/or a lower module. The wearable device may be worn on a user's body such that one or more sensors of the upper and lower modules contact a targeted area of tissue. In one implementation, the wearable device is a watch, band, or strap that can be worn on the wrist of a user such that the upper and lower modules are each in contact with a side of the wrist.

In an embodiment, the wearable device can be a lower module that can be attached to another device. For example, the wearable device can be a lower module that is a clip and/or an add-on to a watch or another wearable device. For example, the lower module may be attachable to the bottom of a watch such that the lower module is in contact with the skin of the wearer.

Each of the upper and lower modules may comprise one or more sensors, including but not limited to optical/PPG sensors, ECG sensors/electrodes, bio impedance sensors, galvanic skin response sensors, tonometry/contact sensors, accelerometers, pressure sensors, acoustic sensors, electromechanical movement sensors, and/or electromagnetic sensors. In one implementation, one or more optical/PPG sensors may comprise one or more light sources for emitting light proximate a targeted area of tissue and one or more optical detectors for detecting either reflected light (where an optical detector is located on the same side of the targeted area as the light source(s), i.e., within the same module) or transmitted light (where an optical detector is located opposite the light source(s), i.e., within an opposing module).

In a further aspect, the strap or band of the wearable device may be configured so as to facilitate proper placement of one or more sensors of the upper and/or lower modules while still affording the user a degree of comfort in wearing the device. In one implementation, rather than a strap that lies in a plane perpendicular to the longitudinal axis of the user's wrist or arm (as is the case with traditional wrist watches and fitness bands), the band may be configured to traverse the user's wrist or arm at an angle that brings one or more components of the upper or lower modules into contact with a specific targeted area of the user while allowing another portion of the band to rest at a position on the user's wrist or arm that the user finds comfortable.

In another aspect, the precise location of the upper and/or lower modules can be customized such that one or more sensors of either module can be placed in an ideal location of a user, despite the physiological differences between body types from user to user.

The aforementioned features result in more comfortable wearable device while also increasing reliability and accuracy of the device sensing, measuring, analyzing, and displaying of physiological information.

In one implementation, the physiological information sensed, measured, analyzed, or displayed can include but is not limited to heart rate information, ECG waveforms, calorie expenditure, step count, speed, blood pressure, oxygen levels, pulse signal features, cardiac output, stroke volume, and respiration rate. In further implementations, the physiological information may be any information associated with a physiological parameter derived from information received by one or more sensors of the wearable device. Regardless, the physiological information may be used in the context of, for example, health and wellness monitoring, athletic training, physical rehabilitation, and patient monitoring. Of course, these examples are only illustrative of the possibilities and the device described herein may be used in any suitable context.

Other aspects of this disclosure relate to predicting a prediction value (such as a blood pressure change value, or simply the change in blood pressure, of a user) using a machine-learning (ML) model that is trained using imbalanced data. Even in cases where the ML model is trained using balanced data, the techniques disclosed herein can lead to better (e.g., more accurate) predictions of the prediction value. To be more specific, the ML model described herein predicts a change in the blood pressure of the user as compared to an initial (e.g., baseline) value.

Imbalanced data and the associated problems are first described.

In a traditional approach to assessing the changes in a continuous signal (e.g., the change to blood pressure) in real-time, a solution is to select a calibration window (e.g., an initial window, a baseline window, etc.) in the beginning of the measurement and an estimation window (e.g., a current window, a current time, an assessment window, etc.) in real-time. The changes in predictor variables can be used to assess the changes in the target continuous signal. The changes in the predictor variables can be used as input to a model that outputs the change in the continuous signal.

To illustrate, during a calibration window (e.g., an initial time window) of a wearable device that is used for estimating the blood pressure of a user, the user may be asked to provide a baseline blood pressure value to the wearable device or to a device that is in communication with the wearable device. The baseline blood pressure may be obtained by the user using traditional blood pressure measurement techniques and instruments (e.g., an ECG device, a sphygmomanometer, other Korotkov-sounds-based device or technique). The calibration can have, or can be at, different frequencies. In an example, the calibration window can be a one-time calibration window, such as at an initial setup time of a wearable device after the user purchases the wearable device. In an example, the calibration window can have a recurring frequency (e.g., daily, such as every morning, weekly, or some other frequency). In an example, the calibration can be explicitly initiated by the user at any time.

The baseline blood pressure value can be provided to the wearable device (which can be a wearable device as described herein). Baseline features can be extracted from sensor data of sensors of the wearable device. The baseline features can be stored (e.g., correlated) with the baseline blood pressure. At different time points (e.g., time windows), current features are extracted from sensor data of the wearable device. Differences (e.g., pair-wise differences) between the baseline features and the current features can be used as inputs to the ML model, which can output a change in the blood pressure. The pair-wise feature differences can be the change to the predictor variables. The ML model outputs a blood pressure change estimate, which can be a positive or a negative value. The blood pressure change estimate can be added to the baseline blood pressure to obtain an estimate of the current blood pressure of the user.

The above traditional approach suffers from several limitations including a when the calibration window is noisy and training data is imbalanced. If the selected calibration window had a noisy signal, the changes in predictor values can have a low Signal-to-Noise-Ratio (SNR), which can lead to an inaccurate estimation of the changes in the target signal. Imbalanced data is a known issue in most machine learning problems. Extreme changes in the target signal might not happen often. As a result, the training data of the ML model may include little information about such changes. This can cause, in at least some situations, inaccurate predictions.

When applying ML algorithms on an imbalanced dataset, majority classes tend to dominate the learning process. This can result in a poor generalization performance on unknown testing samples. A ML model that is trained with imbalanced data may not be able to identify test samples from minority classes efficiently. A majority class refers to a class for which many data samples exist in the training data set of the ML model. On the other hand, the training data set includes few data samples of a minority class.

To illustrate, to train a ML model to predict (e.g., estimate) changes in blood pressure based on changes in predictive variables (e.g., changes in features extracted from sensor data of a wearable device), sample data may be collected from sample subjects. For example, measured blood pressures and features from sensor data can be used to train the ML model. More specifically, differences in the measured blood pressure values and corresponding differences in feature values can be used to train the ML model. In an example, training data are collected from subjects who are asked to follow a certain protocol. The subjects were asked to perform actions during which training data were collected. The actions include resting, raising an arm, raising a leg, and so on. The increase in blood pressure due to the different actions can be different in different subjects. The change can vary from 15 mmHg to 60 mmHg. Due to this variation, less training data is available for higher changes in blood pressure. As such, higher changes in the blood pressure may be significantly under represented in the training data. This leads to imbalanced training data since large changes in blood pressure values are under-represented in the training data. For example, the training data set may include 1,000 training samples where the change in blood pressure does not exceed 5 mmHg, but only 30 training samples where the change in blood pressure is greater than 20 mmHg. Collecting sufficient data until no data values are under represented may not be possible or feasible. To illustrate, when training data were collected from 140 subjects over a 20-hour period, only in two of the subjects the blood pressure showed an increase of 60 mmHg. In the 20 hours of data collection, only about six minutes of information were obtained for +60 mmHg change in blood pressure.

Implementations according to this disclosure can result in more accurate predictions in machine learning, especially when the ML model is trained using imbalanced data. Different ways can be used to calculate the changes between a calibration point (e.g., a baseline window, baseline time point) and the estimation point (e.g., a current time window).

As an example, consider a continuous signal that is broken down into three blocks in time (e.g., three time points): a first block, a second block, and a third block. The first block can be the baseline window and the third block can be the estimation (e.g., assessment) window. The assessment window is the window in which the change in the prediction value (e.g., the change in blood pressure) is to be estimated. There are two ways to estimate the changes between the first block and the third block. In the first way, the changes of predictors between the first block and the third block can be directly used to predict (e.g., estimate) a value in the third block. In the second way, the changes of predictors between the first block and the second block can be used to obtain a first predicted value, the changes of predictors between the second block and the third block can be used to obtain a second predicted value, and the first predicted value and the second predicted value can be combined to obtain the estimated value for the third block. As such, the changes between the first block and the second block and the changes between the second block and the third block can be estimated and combined to obtain the changes between the first block one the third block. Finally, the predicted values obtained using the first way and the second way can be combined to obtain an assessment (e.g., an estimate, a prediction) of the changes between the first block and the second block.

As further described below, implementations according to this disclosure can be said to generate new data from known data in order to improve prediction accuracy. That is, implementations according to this disclosure can increase the number of estimations for a change and analyze the distribution of the estimations to calculate a more accurate estimation. While implementations are described with respect to estimating changes in blood pressure, it can be readily appreciated that the techniques described herein can be used with any time series data, especially those that involve imbalanced data. The techniques described herein can be used to improve the performance of any machine-learning model that estimates the changes of a continuous signal over time. Several advantages can be achieved.

One advantage is that the effect of noise on measurements can be reduced. That is, the techniques described herein can result in numerous ways to move from one window to another window in time. If one of the time windows has a low SNR, combining the different ways can reduce the impact of the noisy window.

Another advantage is that sensitivity to the unbalanced data can be reduced. The distribution of the training data can be used to determine how the target value (i.e., a to-be-estimate value) is distributed. Usually a range of target values is well represented in the training data. This means that estimated values that fall in the well-represented range, are more accurate than other estimated values. The distribution of the estimated values can be used in selecting the ways that can be used to move from one window to the other. If way X (i.e., path X) consists of parts (i.e., data hops or, equivalently, time hops) that result in target values which are well represented in the training data, then there is a higher possibility that way X provides a more accurate estimate than other ways (e.g., paths). This information can be used to combine the results from different paths to estimate the change in the target between two different windows.

While the systems and devices described herein may be depicted as wrist worn devices, one skilled in the art will appreciate that the systems and methods described below can be implemented in other contexts, including the sensing, measuring, analyzing, and display of physiological data gathered from a device worn at any suitable portion of a user's body, including but not limited to, other portions of the arm, other extremities, the head, and/or the chest.

Reference will now be made in detail to certain illustrative implementations, examples of which are illustrated in the accompanying drawings. Wherever possible, the same reference numbers will be used throughout the drawings to refer to the same or like items.

FIG. 1 depicts an illustrative implementation of an apparatus 100. In one aspect, apparatus 100 may be a physiological monitor worn by a user to sense, collect, monitor, analyze, and/or display information pertaining to one or more physiological parameters. In the depicted implementation, apparatus 100 may comprise a band, strap, or wrist watch. In further implementations, apparatus 100 may be any wearable monitor device configured for positioning at a user's wrist, arm, another extremity of the user, or some other area of the user's body.

In another aspect, apparatus 100 may comprise at least one of an upper module 110 or a lower module 150, each comprising one or more components and/or sensors for detecting, collecting, processing, and displaying one or more physiological parameters of a user and/or other information that may or may not be related to health, wellness, exercise, or physical training sessions.

In addition to upper module 110 and lower module 150, apparatus 100 may comprise a strap or band 105 extending from opposite edges of each module for securing apparatus 100 to the user. In one implementation, band(s) 105 may comprise an elastomeric material. In alternative implementations, band(s) 105 may comprise some other suitable material, including but not limited to, a fabric or metal material.

Upper module 110 or lower module 150 may also comprise a display unit (not shown) for communicating information to the user. The display unit may be an LED indicator comprising a plurality of LEDs, each a different color. The LED indicator can be configured to illuminate in different colors depending on the information being conveyed. For example, where apparatus 100 is configured to monitor the user's heart rate, the display unit may illuminate light of a first color when the user's heart rate is in a first numerical range, illuminate light of a second color when the user's heart rate is in a second numerical range, and illuminate light of a third color when the user's heart rate is in a third numerical range. In this manner, a user may be able to detect his or her approximate heart rate at a glance, even when numerical heart rate information is not displayed at the display unit, and/or the user only sees apparatus 100 through his or her peripheral vision.

In addition, or alternatively, the display unit may comprise a display screen for displaying images or characters to the user. The display unit may further comprise one or more hard or soft buttons or switches configured to accept input by the user.

Apparatus 100 may further comprise one or more communication modules. In some examples, each of upper module 110 and lower module 150 comprise a communication module such that information received at either module can be shared with the other module.

One or more communication modules can also be configured to communicate with other devices such as the user's cell phone, tablet, or computer. Communications between the upper and lower modules can be transmitted from one module to the other wirelessly (e.g., via Bluetooth, RF signal, WiFi, etc.) or through one or more electrical connections embedded in band 105. In a further implementation, any analog information collected or analyzed by either module can be translated to digital information for reducing the size of information transfers between modules. Similarly, communications between either module and another user device can be transmitted wirelessly or through a wired connection, and translated from analog to digital information to reduce the size of data transmissions.

As shown in FIG. 1, lower module 150 can comprise an array of sensors 155 including but not limited to one or more optical detectors 160, one or more light sources 165, and one or more contact pressure/tonometry sensors 170. These sensors are only illustrative of the possibilities, however, and lower module may comprise additional or alternative sensors such as one or more acoustic sensors, electromagnetic sensors, ECG electrodes, bio impedance sensors, galvanic skin response sensors, and/or accelerometers. Though not depicted in the view shown in FIG. 1, upper module 110 may also comprise one or more such sensors and components on its inside surface, i.e. the surface in contact with the user's tissue or targeted area.

In some implementations, the location of sensor array 155 or the location of one or more sensor components of sensor array 155 with respect to the user's tissue may be customized to account for differences in body type across a group of users. For example, band 105 may comprise an aperture or channel 175 within which lower module 150 is movably retained. In one implementation, lower module 150 and channel 175 can be configured to allow lower module 150 to slide along the length of channel 175 using, for example, a ridge and groove interface between the two components. In this manner, and as described in more detail below, where the user desires to place one more components of sensor array 155 at a particular location on his or her wrist, lower module 150 can be slid into the desired location along band 105. Though not depicted in FIG. 1, band 105 and upper module 110 can be similarly configured to allow for flexible or customized placement of one or more sensor components of upper module 110 with respect to the user's wrist or targeted tissue area.

In addition to the sensors and components proximate or in contact with the user's tissue, upper module 110 and/or lower module 150 may comprise additional sensors or components on their respective outer surfaces, i.e. the surfaces facing outward or away from the user's tissue. In the implementation depicted in FIG. 1, upper module 110 comprises one such outward facing sensor array 115. In one implementation, sensor array 115 may comprise one or more ECG electrodes 120. Similar to the sensor arrays of the upper and lower modules proximate or in contact with the user's tissue, outward facing sensor array 115 may further comprise one or more contact pressure/tonometry sensors, photo detectors, light sources, acoustic sensors, electromagnetic sensors, bio impedance sensors, galvanic skin response sensors, and/or accelerometers.

The outward facing sensors of sensor array 115 can be configured for activation when touched by the user (with his or her other hand) and used to collect additional information. For example, where lower module 150 comprises one or more optical detectors 160 and light sources 165 for collecting PPG and heart rate information of the user, outward facing sensor array 115 of upper module 110 may comprise ECG electrodes 120 that can be activated when the user places a fingertip in contact with the electrodes. While the optical detectors 160 and light sources 165 of lower module 150 can be used to continuously monitor blood flow of the user, outward facing sensor array 115 of upper module 110 can be used periodically or intermittently to collect potentially more accurate blood flow information which can be used to supplement or calibrate the measurements collected and analyzed by inward facing sensor array 155 of lower module 150.

In addition to the sensor components described above with respect to each module, each module may further comprise other components for receiving, storing, analyzing, and/or transmitting physiological information. Some of those components are described below with respect to FIG. 8.

Figure 2:
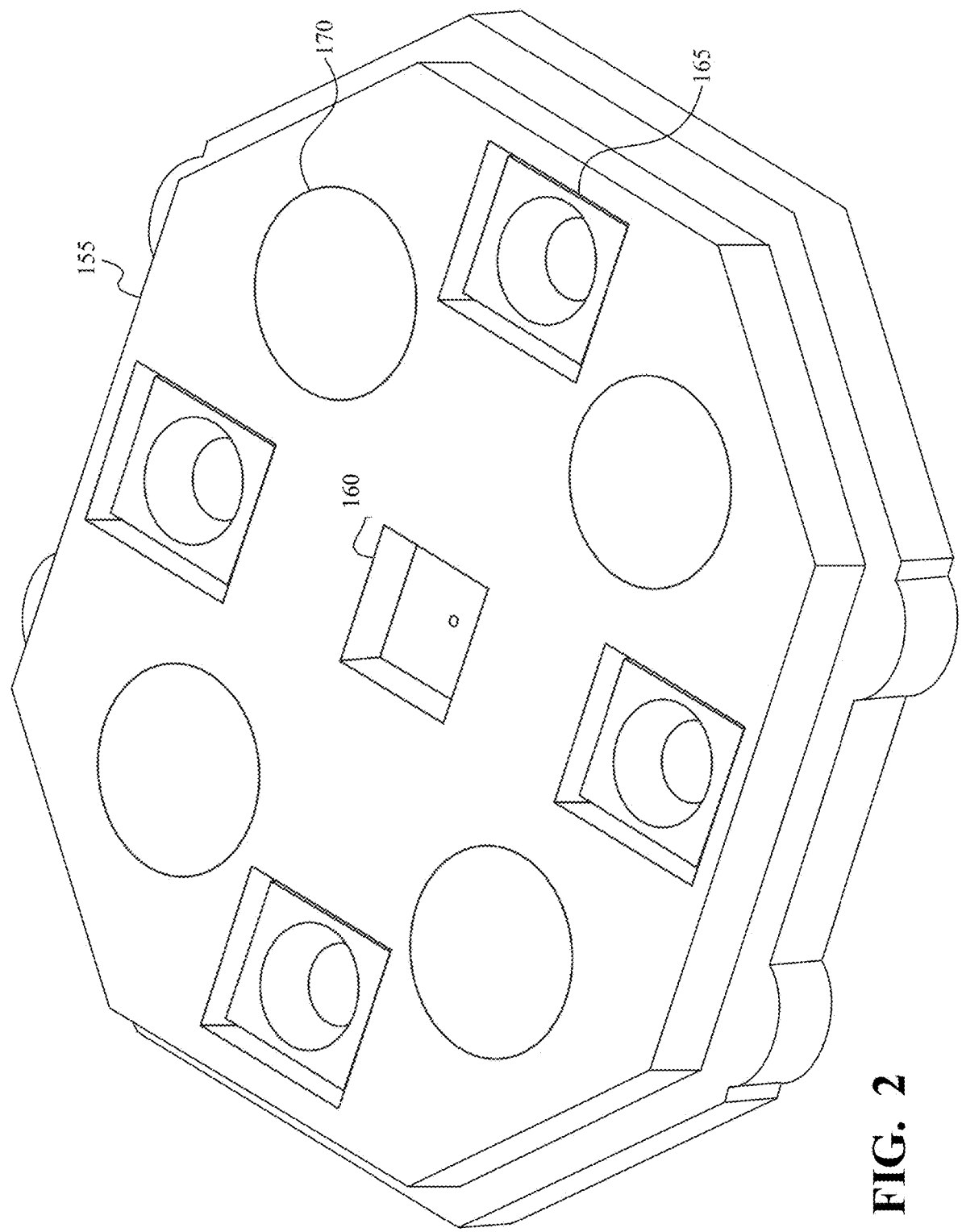
FIG. 2 depicts some aspects of an illustrative implementation of an apparatus as described herein.

FIG. 2 depicts one implementation of inward facing sensor array 155 of lower module 150. As shown, sensor array 155 can comprise sensors including but not limited to one or more optical detectors 160, one or more light sources 165, and one or more contact pressure/tonometry sensors 170. These sensors are only illustrative of the possibilities, however, and sensor array 155 may comprise additional or alternative sensors such as one or more acoustic sensors, electromagnetic sensors, ECG electrodes, bio impedance sensors, galvanic skin response sensors, and/or accelerometers. Upper module 110 may comprise a similar inward facing sensor array (not depicted in FIG. 1) configured to position sensors proximate or in contact with the outside portion of a user's wrist or arm. In some implementations, sensor components of the upper and lower modules 110, 150 can be used in combination to collect and analyze physiological information. For example, and as described in more detail below, one or more light sources of lower module 150 can be used to transmit light through a targeted area of the user's tissue (e.g., a portion of the user's wrist) and the transmitted light can be detected by one or more photodetectors of an inward facing sensor array of upper module 110. In such an implementation, opposing modules 110 and 150 can be used to detect and analyze either reflected or transmitted light.

Figure 3:
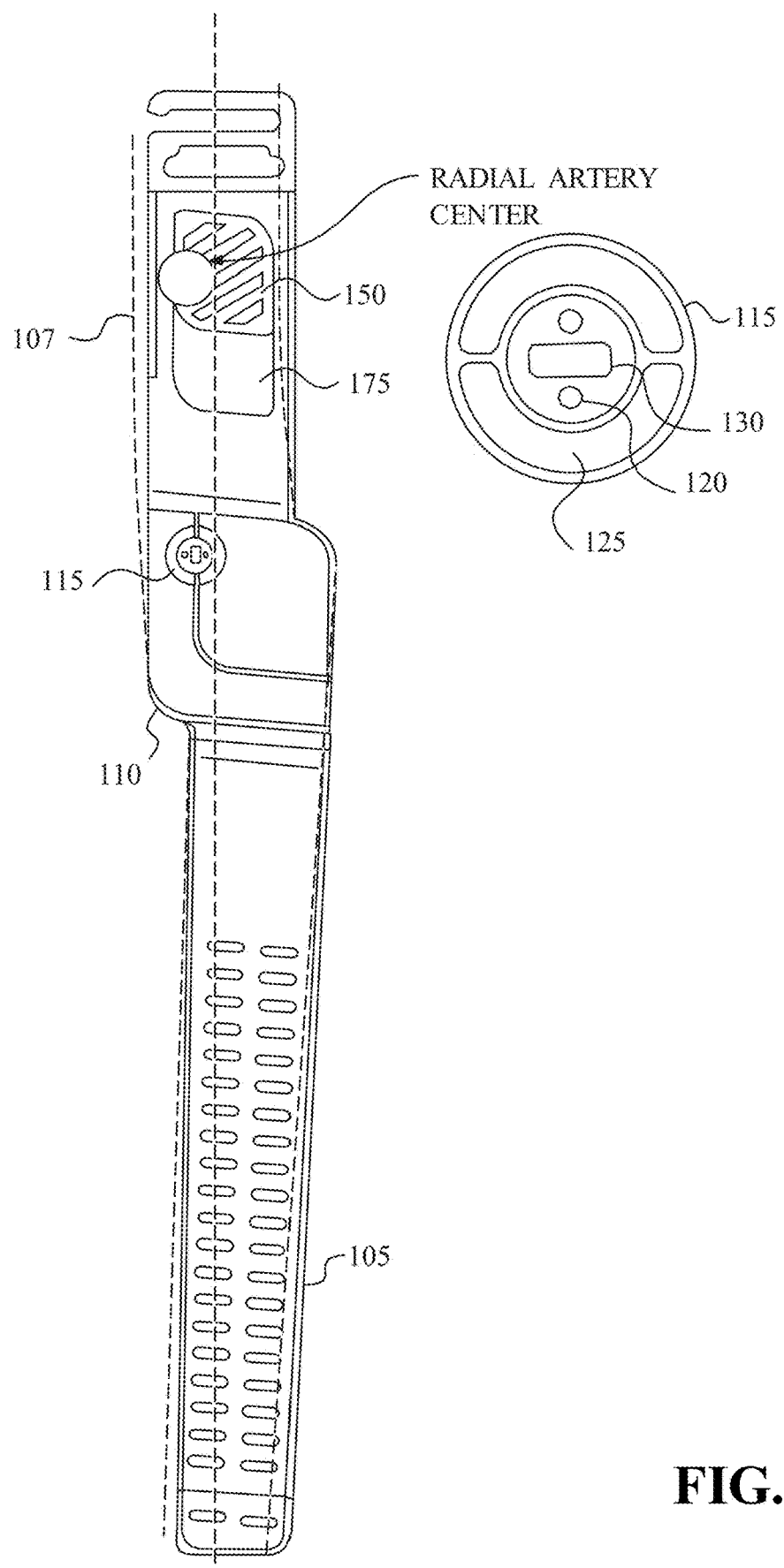
FIG. 3 depicts some aspects of an illustrative implementation of an apparatus as described herein.

FIG. 3 depicts another view of apparatus 100 comprising band 105, upper module 110, and lower module 150. As described above, lower module 150 can be placed within channel 175 of band 105 such that lower module 150 can slide along the longitudinal axis of band 105. The movability of lower module 150 (or upper module 110 in alternative implementations) with respect to band 105 allows a user to customize the location of the inward facing sensors of lower module 150 with respect to a targeted tissue area to ensure reliable and accurate detection of physiological parameters. For example, a user can ensure that the inward facing sensors of lower module 150 are place in a location proximate the center of the user's radial artery.

In another aspect, band 105 may not extend around the user's wrist such that it traverses a circumferential path lying in a plane perpendicular to the longitudinal axis of the user's wrist or arm. Rather, the longitudinal axis of band 105 extends at an angle such that portions of inward facing sensor arrays of upper or lower modules 110, 150 can be placed at suitable locations proximate a desired targeted area of tissue while a portion of band 105 is in contact with portions of the user's wrist or arm that the user finds comfortable (i.e., above or below the wrist joint). In some implementations, where a circumferential path around a user's wrist resides in a plane perpendicular to the longitudinal extension of the user's arm or wrist, band 105 may be set at an angle 107 with respect to the perpendicular plane. In some implementations, angle 107 may be between 5° and 15° with respect to the perpendicular plane. In other implementations, angle 107 may be less than 5° or more than 15°. Of primary importance is the placement of one or more components of the sensor arrays of upper and lower modules 110, 150 proximate or in contact with a desired targeted area of tissue while allowing a portion of band 105 to be worn at a comfortable location off the user's wrist joint. Additional details regarding proper or desirable placement of one or more sensors with respect to targeted tissue areas of a user are described below with respect to other figures.

FIG. 3 also shows a closer view of outward facing sensor array 115. In the implementation depicted, sensor array 115 may comprise one or more ECG electrodes 120 for establishing an electrical connection with a user's fingertip and collected ECG data. Sensor array 115 may further comprise one or more contact pressure/tonometry sensors 125 for detecting the presence of the user's fingertip, which can trigger activation of the ECG electrodes 120. Sensor array 115 may also comprise additional or alternative components 130 such as one or more optical detectors, light sources, acoustic sensors, electromagnetic sensors, bio impedance sensors, galvanic skin response sensors, and/or accelerometers.

Figure 4B:
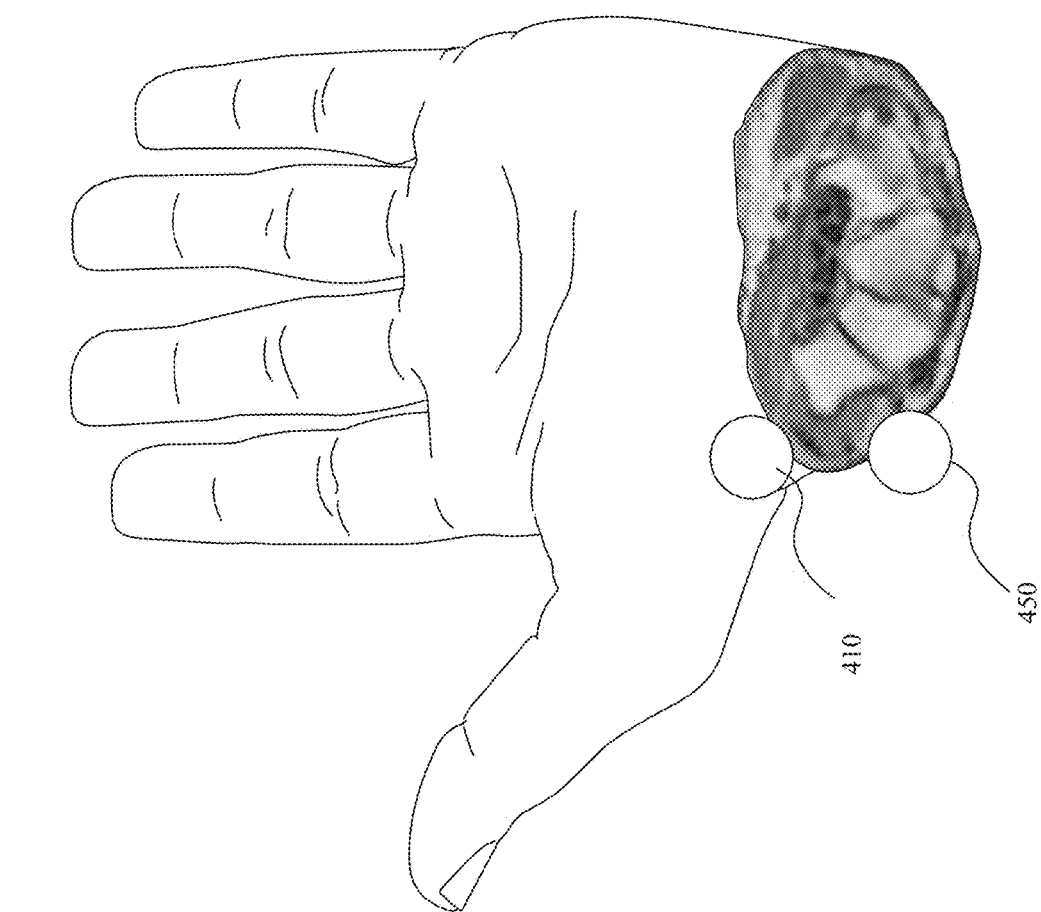
FIGS. 4A-4B depict some aspects of a user's anatomy as described herein.
Figure 4A:
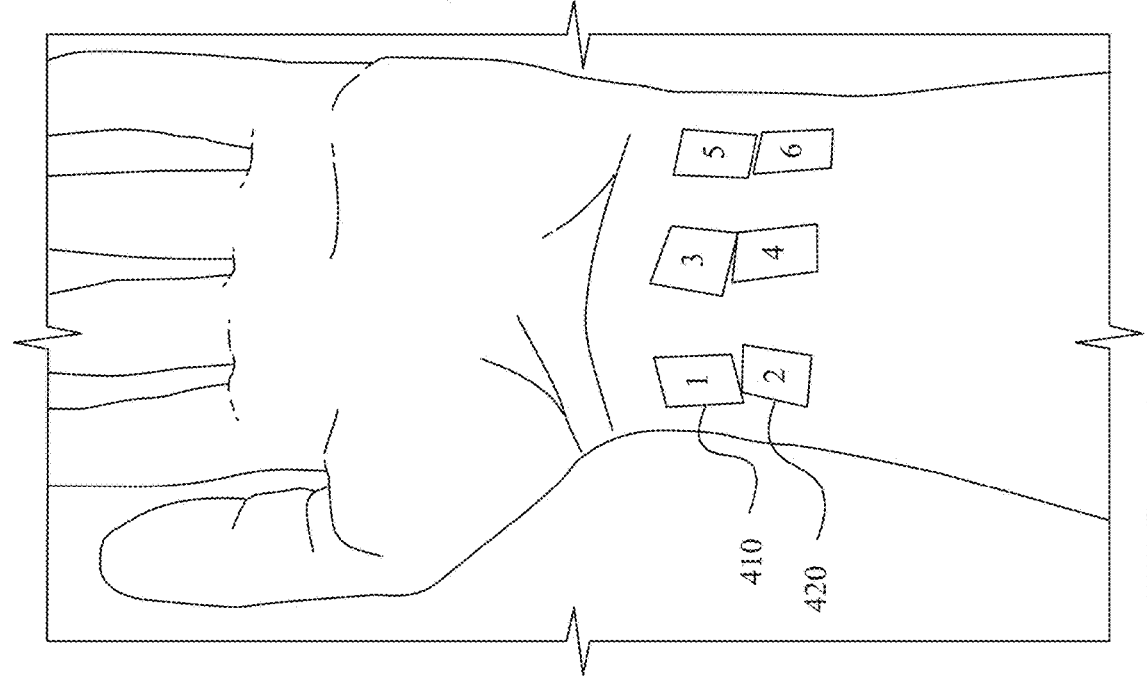

FIG. 4A depicts some points of interest on a human wrist. The best point on the wrist for detecting blood flow, for example in calculating heart rate, blood pressure, respiratory rate, etc., is at a location coinciding with the wrist joint, approximately at location 1 shown as item 410. This location is proximate the radial artery and is referred to as the CUN location.

Thus, the ideal location for a user to wear a wrist worn device is along the line across a line comprising locations 1-3-5. However, for comfort, most users prefer to wear straps or bands off the wrist joint, for example, across locations 2-4-6 shown as item 420. The result is that in most cases, users wear their monitors and corresponding sensors at a location on their wrist or arm that is not ideal and likely to introduce errors in the detection of physiological parameters.

The angle 107 of the band described with respect to FIG. 3 cures this deficiency in that it allows one or more sensor components of lower module 150 to be located above the CUN location while allowing a portion of the remaining band and/or upper module 110 to be positioned at a more comfortable location on the user's wrist or arm, such as line 2-4-6 (item 420).

Further ensuring that one or more sensors of lower module 150 can be placed at a desirable location above the CUN location, and as described in more detail above with respect to FIGS. 1 and 3, lower module 150 can slide along band 105. This allows the user to make further adjustments to the location of one or more sensors, not just along the longitudinal extension of the user's arm when apparatus 100 is in use, but also along the circumferential extension of band 105 while apparatus 100 is in use. Thus, the combination of band 105 extending around the user's wrist at an angle 107 together with the ability to slide the lower module 150 along band 105, ensure the sensors of lower module 150 can be placed at an ideal location with respect to each user (even users of different body types and physical attributes) and that the physiological parameters detected and analyzed by apparatus 100 are collected as accurately as possible.

Not only is apparatus 100 configured so as to ensure proper placement of one or more sensors and comfortability of band 105, but it also may contain additional sensors, such as a pressure sensor, at locations of apparatus 100 other than upper and lower modules 110, 150.

For example, apparatus 100 may comprise a pressure sensor located somewhere else along band 105 or at a latch that secures opposing ends of band 105 around a user's wrist for detecting pressure. Such a sensor can be used to ensure that the user is wearing the apparatus 100 tightly enough to ensure one more other sensors are in sufficient contact with a targeted area of the user's tissue to collect accurate physiological information. In alternative implementations, one or more pressure sensors of the upper and/or lower modules 110, 150 can be used to make the same determination. In either case, apparatus 100 may also be configured to alert the user (for example, via the display unit of upper module 110) if apparatus 100 is being worn too loosely or too tightly to ensure accurate measurements.

FIG. 4B depicts one example of desirable locations for one or more sensors to be placed with respect to a user's wrist or other targeted area. In one implementation, one or more sensors of lower module 150 can be placed adjacent or proximate the item 410 (i.e., the CUN location) and one or more sensors of upper module 110 can be placed opposite the item 410 at point 450 of the user's wrist or targeted area. Such a configuration provides the aforementioned benefits associated with proper placement of sensors over the CUN location, but also allows for apparatus 100 to detect, collect, and analyze blood flow through the radial artery using either reflective or transmissive systems.

Wrist worn PPG sensors currently use a reflective system whereby a sensor array comprises one or more light sources and one or more optical detectors, located near one another and on the same side of a user's targeted area. The one or more light sources of the sensor array illuminate a portion of the user's tissue and light is reflected back to the optical detector(s) of the sensor array. The reflected light detected by the optical detector can be analyzed to estimate physiological parameters such as blood flow and pulse rate.

However, reflective systems may not be as accurate as transmissive systems that place one or more light sources on one side of a user's body and optical detectors on an opposing side of the user's body. One example of a transmissive system are fingertip monitors used in a clinical setting. The monitors are clipped to a patient's fingertip, one side comprising a light source for illuminating the top or bottom of the patient's fingertip, the other side comprising an optical detector for detecting the light transmitted through the fingertip.

It has been thought that transmissive systems are not practical for wrist worn health monitors (or monitors worn at other locations on a user's arm or body) because the wrist is too thick for light that enters one side of a targeted area to be transmitted all the way through to the other side. However, apparatus 100 solves this problem by taking advantage of the natural location of the CUN location (the location of the radial artery at the wrist) at the inside of the wrist just under the thumb. As shown in FIGS. 5A, 5B, and 5C, apparatus 100 can be configured to place the lower module 150 comprising a light source (and/or optical detector) at the location of the CUN artery on the underside of the wrist and place the upper module 110 comprising an opposing optical detector (or light source) at a location opposite the sensors of the lower module at the periphery of the outside of the wrist just below the thumb. In this manner, the path of light transmitted through the wrist between the sensors of the lower and upper modules travels a shorter distance (shown in FIG. 4B) than if the sensors were located closer to the center of the inside and outside of a user's wrist. As a result, light illuminated from either the upper or lower module can be detected at the opposing module in a manner previously only available in clinical settings and limited to locations on the body such as the fingertip.

As described above, apparatus 100 may comprise a number of components and sensors for detecting physiological information and extracting data from it, such as blood flow, heart rate, respiratory rate, blood pressure, steps, calorie expenditure, and sleep.

Data collected from at least one or more of ECG electrodes/sensors, bio impedance sensors, galvanic skin response sensors, tonometry/contact sensors, accelerometers, pressure sensors, acoustic sensors, and electromagnetic sensors can be used for determining physiological information.

One method for determining the heart rate, respiratory rate, blood pressure, oxygen levels, and other parameters of a user involves collecting a signal indicative of blood flow pulses from a targeted area of the user's tissue. As described above, this information can be collected using, for example, a light source and a photo detector. Some implementations may use multiple light sources and they may be of varying colors (e.g., green, blue, red, etc.). For example, one light source may be an IR light source and another might be an LED light (such as a red LED). Using both an IR light source and a colored LED light (such as red) can improve accuracy as red light is visible and most effective for use on the surface of the skin while IR light is invisible yet effective for penetration into the skin. Such implementations may comprise multiple photo detectors, one or more configured to detect colored LED light (such as red) and one or more configured to detect IR light. These photo detectors (for detecting light of different wavelengths) can be combined into a single photodiode or maintained separate from one another. Further, the one or more light sources and one or more photodetectors could reside in the same module (upper or lower) in the case of a reflective system or the light source(s) could reside in one module while the optical detector(s) reside in the other in the case of a transmissive system.

Figure 6A:
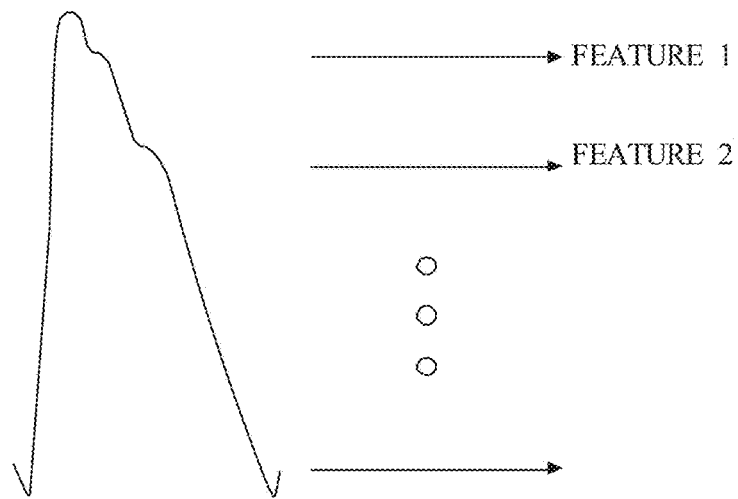
FIG. 6A-6C depict some aspects of an illustrative implementation of an apparatus as described herein.
Figure 6B:
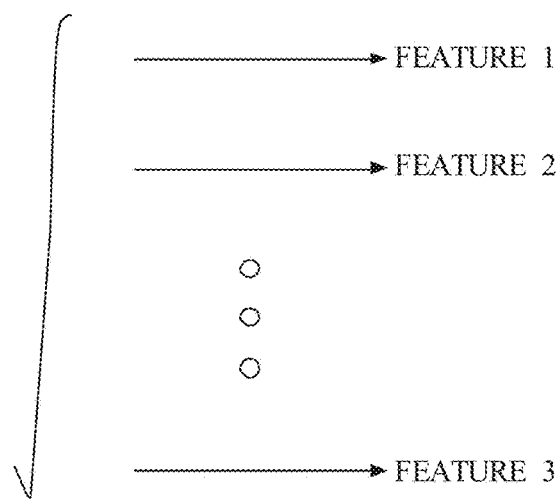
Figure 6C:
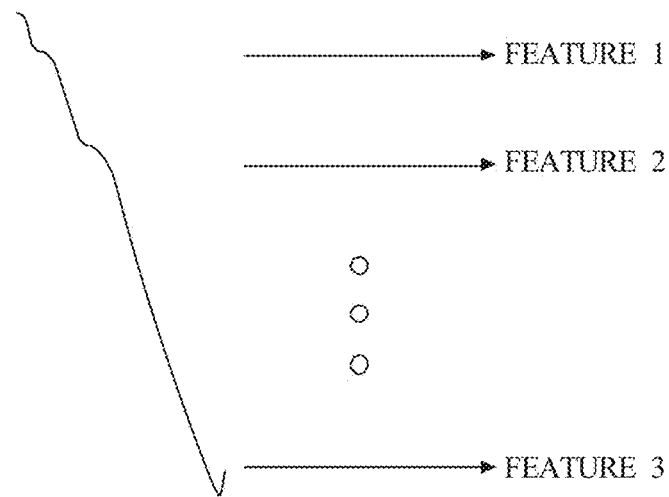

Upon collection of a blood flow pulse signal, a number of parameters can be extracted from both single pulses and a waveform comprising multiple pulses. FIG. 6A depicts a single pulse from which a number of features or parameters can be extracted. Features or parameters extracted from a single pulse can include, but are not limited to, shape of the pulse, a maximum amplitude, a minimum amplitude, a maximum derivative, a time difference between main and secondary peaks, and integral through the entire extraction time (i.e., the area under the pulse). FIGS. 6B and 6C illustrate that even portions of a single pulse can be analyzed for feature extraction. Extracting features at this level of detail has a number of advantages, including the ability to capture a great number of pulse features and store each of those features digitally without having to retain the analog waveform. The result is a savings in storage requirements and ease of data transmission.

Figure 7:
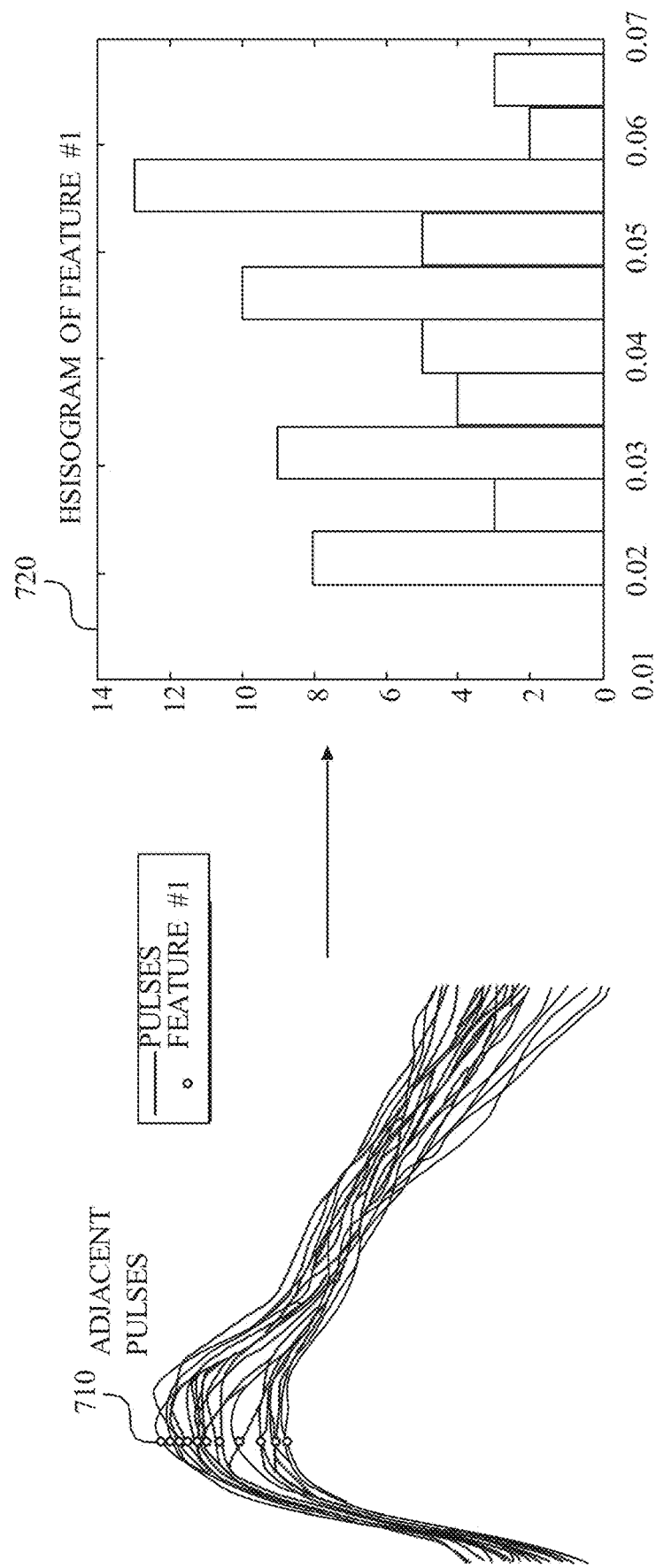
FIG. 7 depicts some aspects of an illustrative implementation of an apparatus as described herein.

Feature extraction can also be performed on a number of pulses or a "pulse train." FIG. 7 depicts a series of pulses overlaid with one another to show the variation among the group with respect to an identified feature. In this manner, the total variation among a series of pulses with respect to a single feature can be determined. The average of a group of pulses with respect to a single feature and the standard deviation of the group with respect to the feature can also be determined. Of course, these are just examples of the types of information that can be collected from a comparison of a single feature over a group of pulses. Moreover, while FIG. 7 depicts the extraction of a single feature from the group of pulses, it should be appreciated that any number of features can be extracted from the group in a manner similar to that described above with respect to a single pulse. FIG. 7 further depicts how information collected about a single feature over a group of pulses can be digitized or presented in a histogram 720.

All of the features or parameters described above, collected using a PPG system comprising one or more light sources and/or one or more optical detectors, can be supplemented with additional sensors such as ECG electrodes/sensors, bio impedance sensors, galvanic skin response sensors, tonometry/contact sensors, accelerometers, pressure sensors, acoustic sensors, and electromagnetic sensors. For example, one or more tonometry/contact sensors can be used to extract tonometry information by measuring the contact vessel pressure. In another example, one or more acoustic sensors comprising a speaker-microphone combination (such as a micro-electro-mechanical system ("MEMS") acoustic sensor) can be used to extract reflected sound pulses from moving vessel walls. Similarly, one or more electromagnetic sensor MEMS can be used to extract voltage induced by coils or magnet pieces pressed to moving vessel walls. In a further implementation, as described above, external or outward facing sensors can be configured to activate when touched by the off-hand (i.e., the hand on which apparatus 100 is not being worn) to collect additional information to help supplement or calibrate the information collected by the inward facing sensors of the upper or lower modules. For example, where internal facing PPG components (i.e., one or more light sources and one or more photo detectors) are used to detect reflected or transmitted light representative of blood flow pulses and some extrapolation of the data is made to determine, for example, heart rate, the user can place a fingertip of his or her off-hand on an outward facing ECG electrode (such as that shown in FIG. 1) to collect a more precise heart rate measurement. The more precise, though of more finite duration, heart rate measurement can be used to aid in the interpretation of the continuous heart rate measurements collected by the inward facing PPG sensors. The outward facing sensor can also comprise other sensors previously described herein, such as one or more contact/tonometry sensors, one or more bio impedance sensors, and one or more galvanic skin response sensors for analyzing electric pulse response. All of the information collected by an outward facing sensor from, for example, the fingertip of the user's off-hand, can be used to refine the analysis of the continuous measurements taken by any one or more of the inward facing sensors.

In addition to the inward and outward facing sensors, apparatus 100 may further comprise additional internal components such as one or more accelerometers and/or gyroscopic components for determining whether and to what extent the user is in motion (i.e., whether the user is walking, jogging, running, swimming, sitting, or sleeping). Information collected by the accelerometer(s) and/or gyroscopic components can also be used to calculate the number of steps a user has taken over a period of time. This activity information can also be used in conjunction with physiological information collected by other sensors (such as heart rate, respiration rate, blood pressure, etc.) to determine a user's caloric expenditure and other relevant information.

To determine a user's blood pressure, the PPG information described above may be combined with other sensors and techniques described herein. In one implementation, determining a user's blood pressure can comprise collecting a heart rate signal using a PPG system (i.e., one or more light sources and photo detectors) and performing feature extraction (described above) on single pulses and a series of pulses. The features extracted from single pulses and series of pulses can include statistical averages of various features across a series, information regarding the morphological shape of each pulse, the average and standard deviation of morphology of a series of pulses, temporal features such as the timing of various features within single pulses, the duration of a single pulse, as well as the average and standard deviation of the timing of a feature or duration of pulses within a series of pulses, and the timing of morphological features across a series of pulses (i.e., the frequency with which a particular pulse shape occurs in a series).

As described above, this feature extraction can not only be performed on a series of pulses and single pulses, but also on portions of a single pulse. In this manner, information pertaining to both systolic and diastolic blood pressure can be ascertained as one or more portions of an individual pulse correspond to the heart's diastole (relaxation) phase and one or more other portions of an individual pulse correspond to the heart's systole (contraction) phase. In some implementations, up to 200 features can be extracted from a partial pulse, a single pulse, and/or a series of pulses. In alternative implementations, fewer or more features may be extracted.

In addition to features extracted from PPG or ECG information, information and features can also be collected by contract/tonometry sensors, pressure sensors, bio impedance sensors galvanic skin response sensors, accelerometers, acoustic sensors, and electromagnetic sensors. For example, pressure sensors or bio impedance sensors can be used to identify blood flow pulses of user and, similar to PPG or ECG data, features can be extracted from the collected data.

The extracted features can then be cross-referenced or compared to entries in a library containing data corresponding to a population of subjects. For each subject, the library may contain information associated with each extracted feature. The library can also contain a direct measured or verified blood pressure for each subject. In further implementations, the library may contain more than one directly measured or verified blood pressure measurement for each subject, each corresponding to a subject in a different condition, such as one corresponding to the subject at rest, one corresponding to the subject engaged in light activity, and one corresponding to the subject engaged in strenuous activity. Thus, the extracted features of the user, as well as activity information pertaining to the user, can be compared to entries in the library to find one or more subjects with which the user's extracted features most closely match and the user's blood pressure can then be estimated based on the verified blood pressure of those subjects.

As one example, when features are extracted from a series of pulses, a standard deviation or range of variation across the series can be ascertained. Generally speaking, a large variation across a series of pulses can be associated with flexible, healthy veins. As a result, individuals exhibiting large pulse-to-pulse variations across a series of pulses typically have relatively low blood pressure. Conversely, little to no variation in features across a series of pulses is typically associated with relatively high blood pressure.

The library described above can be generated by extracting the same features from partial pulses, individual pulses, and series of pulses across hundreds or thousands of subjects. The subjects' verified blood pressure can also be measured such that it can be associated with each feature extracted from the subject's pulse information. The subject entries in the library can also be sorted based on information helpful for estimating blood pressure. For example, subjects in the library can be identified as male or female, belonging to a particular age group, or associated with one or more past health conditions. Individual subjects can be associated with information indicative of the subject's sex, age, weight, race, and any other medically meaningful distinction. Moreover, entries can be associated with information collected by other sensors at the time the verified blood pressure measurement was taken, including information collected by contract/tonometry sensors, pressure sensors, bio impedance sensors galvanic skin response sensors, accelerometers, acoustic sensors, and electromagnetic sensors. As just one example, if a user is determined to be engaged in physical activity (through a combination of accelerometer and heart rate data, as an example), his or her extracted features may only be compared to data in the library corresponding to subjects engaged in similar physical activity. Information pertaining to subjects contained in the library may also be correlated to each subject's resting heart rate, BMI, or some other medically significant indicia. For example, if a user is a young female with a low resting heart rate who is currently engaged in moderate activity, her extracted features should be compared to subjects in the library identified as young females with low resting heart rate whose blood pressure was verified during moderate activity rather than comparing the user's extracted features to an elderly male subject with a relatively high resting heart rate and whose blood pressure was verified during strenuous activity.

When the user's extracted features are compared to features recorded in the library, apparatus 100 can also weigh the entries of subjects most closely corresponding to the user more heavily than entries of subjects associated with indicia different from that of the user. For example, if the user is a male, features extracted from male subjects may be weighed more heavily than female subjects because a particular pulse variation in men of a particular age may correspond to relatively high blood pressure whereas the same pulse variation in women of that particular age may correspond to lower blood pressure.

According to the techniques described herein, accurate blood pressure estimates for a user can be made without requiring direct blood pressure measurement of the user. However, in some implementations, the user's blood pressure estimates can be further calibrated by direct measurement of the user's blood pressure by another device and that verified blood pressure can be input into apparatus 100 to aid in future estimations of the user's blood pressure.

Calibration can also be accomplished with an outward facing ECG sensor.

While an inward facing PPG sensor can continuously or periodically collect heart rate data of a user, occasionally the user may be prompted to place a fingertip of his or her off-hand on an outward facing ECG sensor (e.g., electrodes). The inward facing sensor arrays of apparatus 100 may contain additional electrodes thereby completing an electrical circuit through the user's body and allowing a more precise pulse waveform to be collected. Feature extraction can be performed on these pulses, series of pulses, and partial pulses in the same manner as described above with respect to PPG information and used to cross-reference the library.

In still a further implementation, where apparatus 100 determines, based on its continuous or periodic monitoring of the user's blood pressure using PPG or pressure sensors, that a user's blood pressure is unusually or dangerously high or low, apparatus 100 may prompt the user to place a fingertip of his or her off-hand on an outward facing ECG electrode in order to verify the unusual or unsafe condition. If necessary, apparatus 100 can then alert the user to call for help or seek medical assistance.

As described above, the upper and/or lower modules 110, 150 can be configured to continuously collect data from a user using its inward facing sensor arrays. However, certain techniques can be employed to reduce power consumption and conserve battery life of apparatus 100. For instance, in some implementations, only one of the upper or lower modules 110, 150 may continuously collect information. In alternative implementations, neither module may be continuously active, but may wait to collect information when conditions are such that accurate readings are most likely. For example, when one or more accelerometers or gyroscopic components of apparatus 100 indicate that a user is still, at rest, or sleeping, one or more sensors of upper module 110 and/or lower module 150 may collect information from the user while artifacts resulting from physical movement are absent.

While techniques for estimating a user's blood pressure using pulse signal, pressure, impedance, and other collected and input information has been described above, it should be appreciated that similar techniques can be employed to estimate a user's oxygen levels ($SvO_2$), hydration, respiration rate, and heart rate variability. For example, PPG, ECG, bio impedance, and acoustic measurements taken from the user can be cross-referenced with the aforementioned library and compared to subjects most closely matching the user (e.g., sex, age, height, weight, race, resting heart rate, BMI, current activity level, and any other medically meaningful distinction. Measured or verified hydration levels of one or more subjects can then be used to estimate the hydration level of the user. A similar process can be employed to estimate the user's oxygen levels ($SvO_2$), respiration rate, and heart rate variability.

Figure 8:
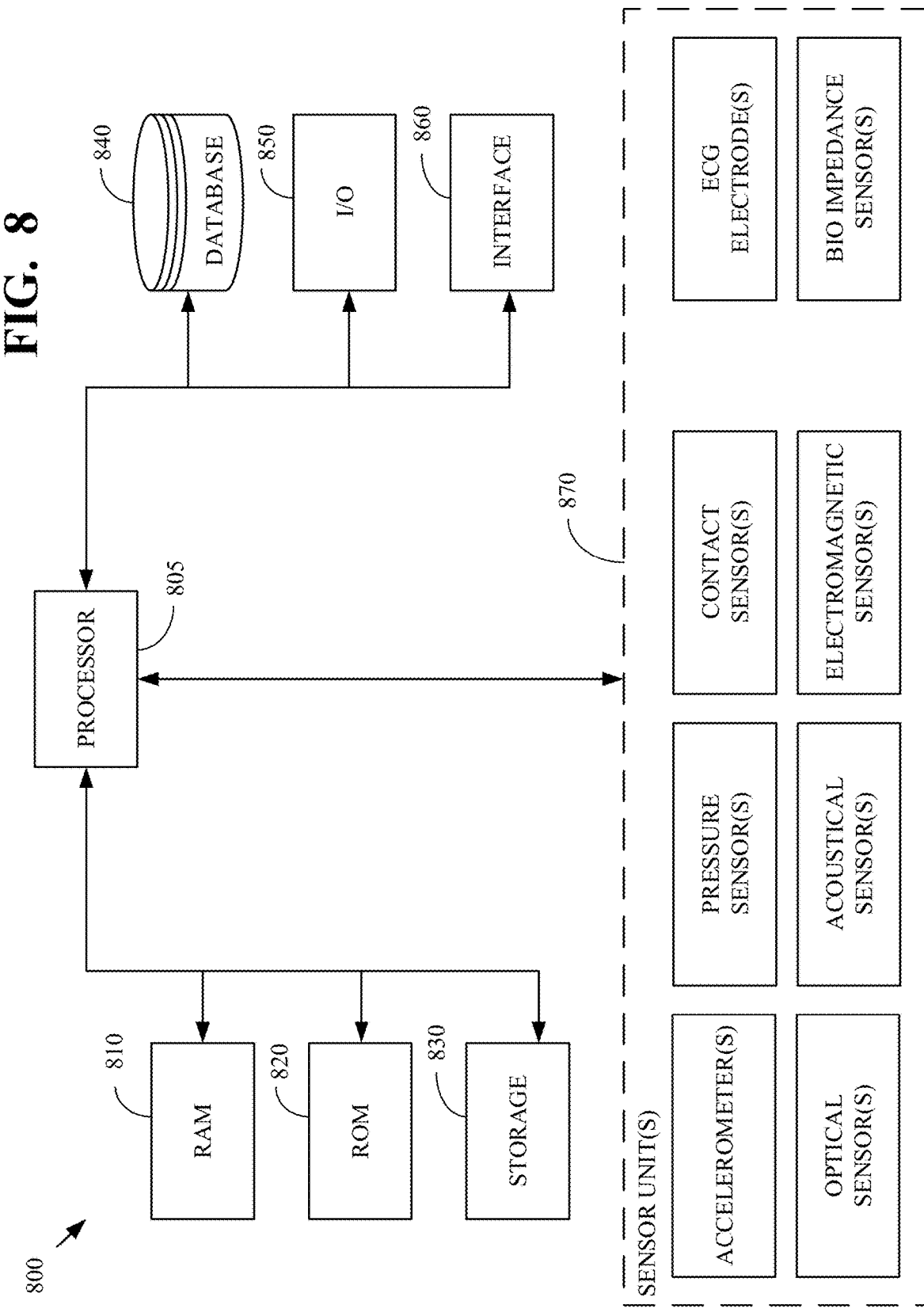
FIG. 8 depicts an illustrative implementation of a computing system as described herein.

FIG. 8 depicts an illustrative processor-based computing system (i.e., a system 800) representative of the type of computing system that may be present in or used in conjunction with any aspect of apparatus 100 comprising electronic circuitry. Each of upper or lower modules 110, 150 may comprise any one or more components of system 800. In some implementations, one module may contain one of the components of system 800 and the other module, rather than comprising a similar component, may be in wired or wireless communication with the component residing in the other first module. Alternatively, each module may comprise a similar component as compared to the other module such that it is not necessary to communication with the first module to enjoy the functionality of the component. For example, upper module 110 may comprise storage, a power source, and/or a charging port, while lower module 150 may have access to the upper module's storage and/or draw power from the power source of the upper module through a wired or wireless connection. Alternatively, each module may have its own storage and/or power source. For the sake of simplicity, the system 800 will be described herein as if it encompasses the components of upper and lower modules 110, 150 collectively, while the reader appreciates that one or more components described herein may reside only in one module or may be found in both modules.

The system 800 may be used in conjunction with any one or more of transmitting signals to and from the one or more accelerometers, sensing or detecting signals received by one or more sensors of apparatus 100, processing received signals from one or more components or sensors of apparatus 100 or a secondary device, and storing, transmitting, or displaying information. The system 800 is illustrative only and does not exclude the possibility of another processor- or controller-based system being used in or with any of the aforementioned aspects of apparatus 100.

In one aspect, system 800 may include one or more hardware and/or software components configured to execute software programs, such as software for storing, processing, and analyzing data. For example, system 800 may include one or more hardware components such as, for example, processor 805, a random access memory module (RAM) 810, a read-only memory module (ROM) 820, a storage system 830, a database 840, one or more input/output (I/O) modules 850, an interface module 860, and one or more sensor modules 870. Alternatively and/or additionally, system 800 may include one or more software components such as, for example, a computer-readable medium including computer-executable instructions for performing methods consistent with certain disclosed implementations. It is contemplated that one or more of the hardware components listed above may be implemented using software. For example, the storage system 830 may include a software partition associated with one or more other hardware components of system 800. System 800 may include additional, fewer, and/or different components than those listed above. It is understood that the components listed above are illustrative only and not intended to be limiting or exclude suitable alternatives or additional components.

Processor 805 may include one or more processors, each configured to execute instructions and process data to perform one or more functions associated with system 800. The term "processor," as generally used herein, refers to any logic processing unit, such as one or more central processing units (CPUs), digital signal processors (DSPs), application specific integrated circuits (ASICs), field programmable gate arrays (FPGAs), and similar devices. As illustrated in FIG. 8, processor 805 may be communicatively coupled to RAM 810, ROM 820, the storage system 830, database 840, I/O module 850, interface module 860, and one more of the sensor modules 870. Processor 805 may be configured to execute sequences of computer program instructions to perform various processes, which will be described in detail below. The computer program instructions may be loaded into RAM for execution by processor 805.

RAM 810 and ROM 820 may each include one or more devices for storing information associated with an operation of system 800 and/or processor 805. For example, ROM 820 may include a memory device configured to access and store information associated with system 800, including information for identifying, initializing, and monitoring the operation of one or more components and subsystems of system 800. RAM 810 may include a memory device for storing data associated with one or more operations of processor 805. For example, ROM 820 may load instructions into RAM 810 for execution by processor 805.

The storage system 830 may include any type of storage device configured to store information that processor 805 may need to perform processes consistent with the disclosed implementations.

Database 840 may include one or more software and/or hardware components that cooperate to store, organize, sort, filter, and/or arrange data used by system 800 and/or processor 805. For example, database 840 may include user profile information, historical activity and user-specific information, physiological parameter information, predetermined menu/display options, and other user preferences. Alternatively, database 840 may store additional and/or different information.

I/O module 850 may include one or more components configured to communicate information with a user associated with system 800. For example, I/O module 850 may comprise one or more buttons, switches, or touchscreens to allow a user to input parameters associated with system 800. I/O module 850 may also include a display including a graphical user interface (GUI) and/or one or more light sources for outputting information to the user. I/O module 850 may also include one or more communication channels for connecting system 800 to one or more secondary or peripheral devices such as, for example, a desktop computer, a laptop, a tablet, a smart phone, a flash drive, or a printer, to allow a user to input data to or output data from system 800.

The interface module 860 may include one or more components configured to transmit and receive data via a communication network, such as the Internet, a local area network, a workstation peer-to-peer network, a direct link network, a wireless network, or any other suitable communication channel. For example, the interface module 860 may include one or more modulators, demodulators, multiplexers, demultiplexers, network communication devices, wireless devices, antennas, modems, and any other type of device configured to enable data communication via a communication network.

System 800 may further comprise one or more sensor modules 870. In one implementation, sensor modules 870 may comprise one or more of an accelerometer module, an optical sensor module, and/or an ambient light sensor module. Of course, these sensors are only illustrative of a few possibilities and sensor modules 870 may comprise alternative or additional sensor modules suitable for use in apparatus 100. It should be noted that although one or more sensor modules are described collectively as sensor modules 870, any one or more sensors or sensor modules within apparatus 100 may operate independently of any one or more other sensors or sensor modules. Moreover, in addition to collecting, transmitting, and receiving signals or information to and from sensor modules 870 at processor 805, any one or more sensors of sensor module 870 may be configured to collect, transmit, or receive signals or information to and from other components or modules of system 800, including but not limited to database 840, I/O module 850, or the interface module 860.

Disclosed herein are also implementations of an apparatus for measuring blood pressure. Traditionally, blood pressure can be derived or calculated from a pulse transmission time (PTT). PTT is typically measured using ECG technologies, or using ECG in conjunction with PPG technologies. In an example of a traditional blood pressure measurement system using PTT, PPG sensors can be used on the palm and the wrist, and ECG sensors actually sense the exact electrical pulse that is due to the pumping action of the heart. Such devices measure the time it takes the blood to travel to the Palm and to the wrist. Based on the user's physiology, the velocity of propagation can also be measured. The velocity of propagation is referred to as the pulse wave velocity (PWV). That is, the PWV measures the time that it takes a pulse released from the heart to reach, for example, the wrist. As is known, PWV is measured over a distance that is significantly longer than the length of sensing modules described herein.

However, implementations of a sensing module according to this disclosure can measure the blood pressure without the use of ECG sensors. Rather, pressure sensors can be used to measure (e.g., estimate, calculate, etc.) the blood pressure. As the sizes (e.g., length) of sensing modules according to this disclosure are relatively small, it cannot be said that PWV can be directly measured using such sensing modules. A pulse front velocity (PFV) is used to estimate the PWV. PFV, and as further described below, refers to the velocity of a blood wave as the blood wave passes under a sensing module.

While the term blood pressure is used throughout, it is to be understood that blood pressure encompasses any measure relating to blood pressure such as a systolic and/or mean and/or diastolic measure. Blood pressure is related to the full shape of pulse pressure. In some cases, a maximum point (the systolic blood pressure) of a pulse cycle and/or the minimum (the diastolic blood pressure) of a pulse cycle can be determined.

Figure 9:
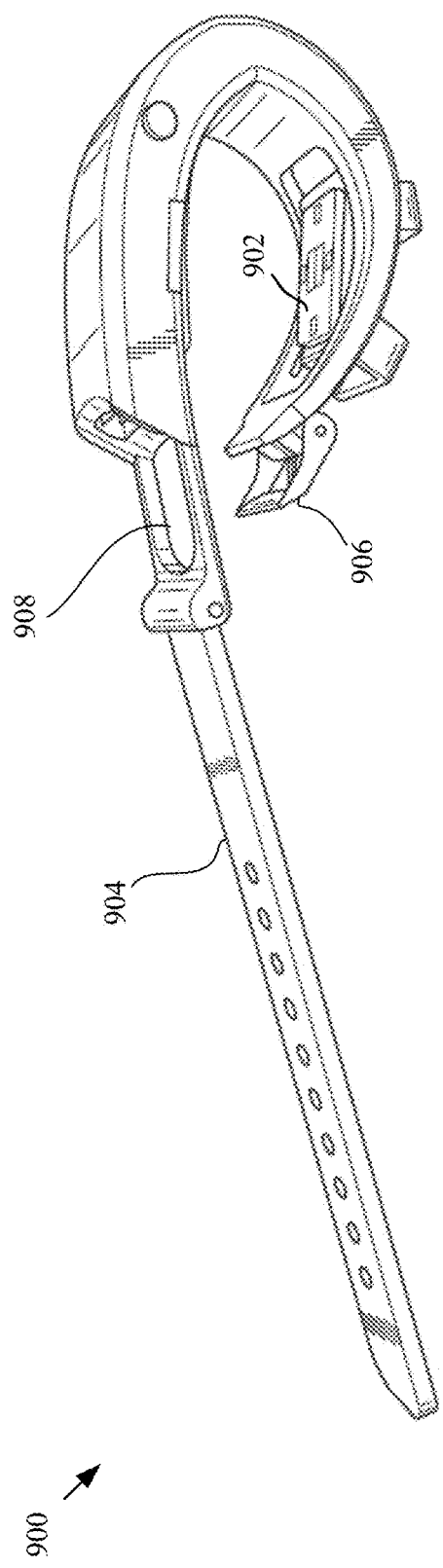
FIG. 9 depicts some aspects of an illustrative implementation of an apparatus as described herein.

FIG. 9 depicts some aspects of an illustrative implementation of an apparatus 900 as described herein. The apparatus 900 can be similar to the apparatus described with respect to the apparatus of FIG. 3. The apparatus 900 includes a lower module 902, which can be as described with respect to the lower module 150 of FIGS. 1 and 2. The lower module 902 may be referred herein as a sensing module, a stage, or other similar terms that will be understood, from the context, to be referring to a sensing module that is similar to the lower module 902.

The apparatus 900 includes an attachment mechanism. The attachment mechanism illustrated in the apparatus 900 includes a strap 904 and a buckle 906. However, other configurations of the attachment mechanism are possible. The attachment mechanism includes an aperture 908. The aperture 908 is intended for receiving the wrist bone of a wearer (i.e., a user). The aperture 908 is intended for comfortable wearing by the user while ensuring, with high probability, that the lower module 902 is optimally placed over the user's radial artery for optimal sensing and measuring of the user's physiological information. As described with respect to FIGS. 4A-4B, the optimal placement is approximately at location 1 shown as item 410.

As can be appreciated, different users prefer the wearing of a wearable device, such as the apparatus 900, at different locations, such as below the wrist bone, above the wrist bone, tightly, loosely, etc. Several aspects of the lower module 902 and the attachment mechanism can be combined to adapt to the user's comfortable and preferred wearing preferences while ensuring that the lower module 902 is placed over the user's radial artery for the most optimal sensing and measurement. For example, the band 904 can extend at an angle, such as described with respect to the angle 107 of FIG. 3. For example, the lower module 902 can slide along the strap 904, as described with respect to the lower module 150 and the band 105 of FIG. 3. For example, the attachment mechanism can include an aperture (such as in a band) for receiving the wrist bone. In another aspect, the lower module 902 can be approximately 20 mm in the longitudinal direction (i.e., the direction of the radial artery) by 17 mm in the lateral direction. The relatively large size of the lower module 902 enables the monitoring of a large surface of the skin (e.g., the radial artery) and/or a large volume (e.g., of blood) inside the wrist. Additionally, a calibration process, which is described above and further described below, can be used to adapt the apparatus 900 to the wearing preferences and/or anatomy of the user.

Figure 10:
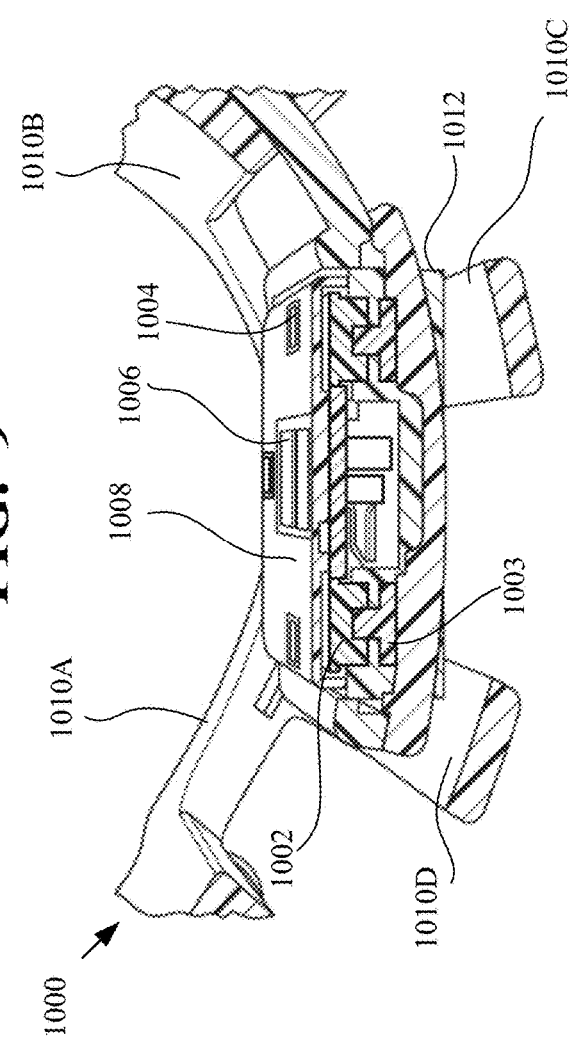
FIG. 10 depicts some aspects of an illustrative implementation of an apparatus as described herein.

FIG. 10 depicts some aspects of an illustrative implementation of a sensing module 1000 as described herein. More specifically, FIG. 10 shows a cross sectional view of the sensing module 1000. The sensing module 1000 can be the lower module 150 of FIG. 1 and FIG. 2. FIG. 10 illustrates a configuration of a pressure sensor 1002, which can be as described with respect to the contact pressure/tonometry sensors 170 of FIG. 2. The pressure sensor 1002 is attached (e.g., fastened, anchored, secured, etc.) to a base 1012 of the sensing module 1000 using a back pin 1003. FIG. 10 includes other parts 1010A-1010D, which may be parts of an attachment mechanism. The other parts 1010A-1010D are not to be considered parts of the sensing module 1000.

The sensing module 1000 includes one or more light sources 1004, as described with respect to the light sources 165 of FIG. 2. The sensing module 1000 includes one or more optical detectors 1006, as described with respect to the optical detectors 160 of FIG. 2. As such, the sensing module 1000 can include multiple sensing technologies. Namely, the sensing module 1000 can include commonly used and known PPG technologies (e.g., optical detectors and/or light sources) and pressure sensors. In an implementation, the sensing module 1000 can include eight LED light sources and two photodiodes. As described above, LEDs that emit light in different wavelengths can be used. For example, some of the LEDs can emit a visible color (e.g. red) while other LEDs can emit an invisible color (e.g., infrared). Such color selection enables the sensing of blood relatively deep into the tissue, thereby enabling the sensing and/or measurement of a relatively large volume of blood.

While the sensing module 1000 is shown as including PPG sensors, in some embodiments, a sensing module, such as the sensing module 1000, may not include any PPG sensors. As such, the sensing module can include, can constitute, or can be a pressure sensor.

It is noted that known PPG sensors that are incorporated in, for example, sports bands and/or sports watches, may use green light. Green light can be suitable for sensing heart rate while a user is in motion (e.g., running, cycling, etc.). However, green light does not penetrate the skin as much as red and/or infrared light. As such, green PPG light sources are not as suitable for blood volume measurements as red and/or infrared PPG light sources. However, as red and infrared light sources are more sensitive to motion, a wearable device according to this disclosure can include motion compensation (e.g., motion canceling) algorithms.

Motion compensation can be performed in cases where the user is determined to be performing an activity. For example, and as described above, a wearable device according to this disclosure can include an accelerometer, a gyroscope, and/or other motion detecting sensors. Information from such motion detecting sensors can be used to determine (e.g., infer, conclude, etc.) that the user is in motion. If the user is determined to be in motion, then motion compensation can be enabled. In some situations, the user may be asked (for example, via messages and/or indicators displayed for the user on a display of the wearable device) to remain at rest while the user's blood pressure is measured. In such situations, motion compensation may not be employed. In yet another situation, even if the user is asked to remain at rest, information from sensors may indicate that the user is in motion. In such situations, motion compensation may be enabled.

The relatively large size of the sensing module 1000 ensures that blood flow in vessels proximal to the radial artery can be observed (e.g., sensed, detected, measured, etc.) by the PPG sensors. Additionally, the relatively large size of the sensing module 1000 enables, as further described below, the measurement of the PFV, from which PWV may be derived.

The sensing module 1000 can include 1 or more pressure sensors. In the case that two pressure sensors are used, they are arranged toward the edges of the sensing module 1000 so as to maximize the distance between them. The two pressure sensors are arranged in the longitudinal direction along the direction of blood flow in the radial artery. In another implementation, three pressure sensors can be used. In yet another implementation, four pressure sensors are used. For example, each of the four pressure sensors can be placed in a corner of the sensing module 1000. Using three or more pressure sensors enables better triangulation of a force epicenter (which is further described with respect to FIG. 11). The PPG sensors and the pressure sensors are arranged such that they do not interfere with each other. For example, the optical sensors (e.g., the light sources 1004 and the optical detectors 1006) have open pathways to the skin that is not obstructed by the pressure sensor; and the ability of the pressure sensor 1002 to detect and measure pressure is not interfered with by the PPG sensors. That is, the pressure sensor 1002 can feel (e.g., is in contact with) the skin. The pressure sensor 1002 can be under (e.g., overlaid by) an interface 1008. The interface 1008 can be a plastic interface, a rubber interface, a silicone interface, a sponge interface, any other interface type, of a combination thereof. It is noted that the pressure sensor 1002 can be compared to a scale component. However, it is noted that such a scale can be in an upside-down configuration. That is, the bottom of the scale can be the part of the scale that touches the skin that is exerting the pressure (e.g., the weight) to be measured.

As the pressure sensor 1002 can be in constant contact with the skin of the user while worn, a wearable device that incorporates that a sensing module such that the sensing module 1000 can continuously measure the user's blood pressure. As such, a computing system, such as the system 800 can use the pressure sensor 1002 for continuous or for episodical measurement of the user's blood pressure. As further described with respect to FIG. 11, blood pressure can be measured by continuously or episodically reconstructing a distribution of forces on the sensing module 1000, as measured the pressure sensor 1002.

It is noted that the pressure sensor 1002 is not limited to one specific type of the pressure sensor. Any suitable pressure sensor or force sensor can be used. For example, the pressure sensor can be a pressure transducer, a piezoelectric electric pressure sensor, a capacitive pressure sensor, an optical pressure sensor, a resistive pressure sensor, a barometric pressure sensor, other pressure sensors, or a combination thereof.

The sensing module 1101 (i.e., the skin movement sensor) can be used for sensing the mechanical movement of the radial artery. More accurately, the sensing module 1101 can be used for sensing the skin movement (e.g., to receive skin movement information) above the radial artery.

In an implementation, the skin movement can be measured (e.g., to receive skin movement information) using optical sensors, rather than, as described above, mechanical sensors. Optical sensors can be more sensitive, more stable, and have more resolution than mechanical force (e.g., pressure) sensors.

A light (such as from an LED source, which can be the same or different LED sources already described above) can be directed at the skin on or near the radial artery. A light sensor (such as a photodiode, which can be the same or different photodiode already described above) can detect the reflected light, which can be modulated by the movement of the skin. Using optical sensors to measure the skin movement can be further enhanced using mechanical components so that the optical sensors can be more sensitive to the skin movement. As such, the skin movement can be transformed to a more magnified and exaggerated mechanical movement, which can be more easily detected using optical sensors.

In one implementation, an elastic and/or reflective material can be used to reflect the light. The elastic and/or reflective material can be affixed to the skin. As such, the material (i.e., a component affixable to the skin) can lightly touch the skin or can be adhered to the skin. Such material can essentially act as a mirror to reflect the light. The elasticity of the material exaggerates the skin movement for better sensing and detectability.

In another implementation, a component that includes a spring or a spring-like mechanism (e.g., a bouncing frame) can be attached to the skin such that blood flow through the artery can cause tension and extension of the spring. As such, a surface of the component that faces the sensing module moves due to the blood flow and such movement can be detected by the optical sensors.

Figure 11:
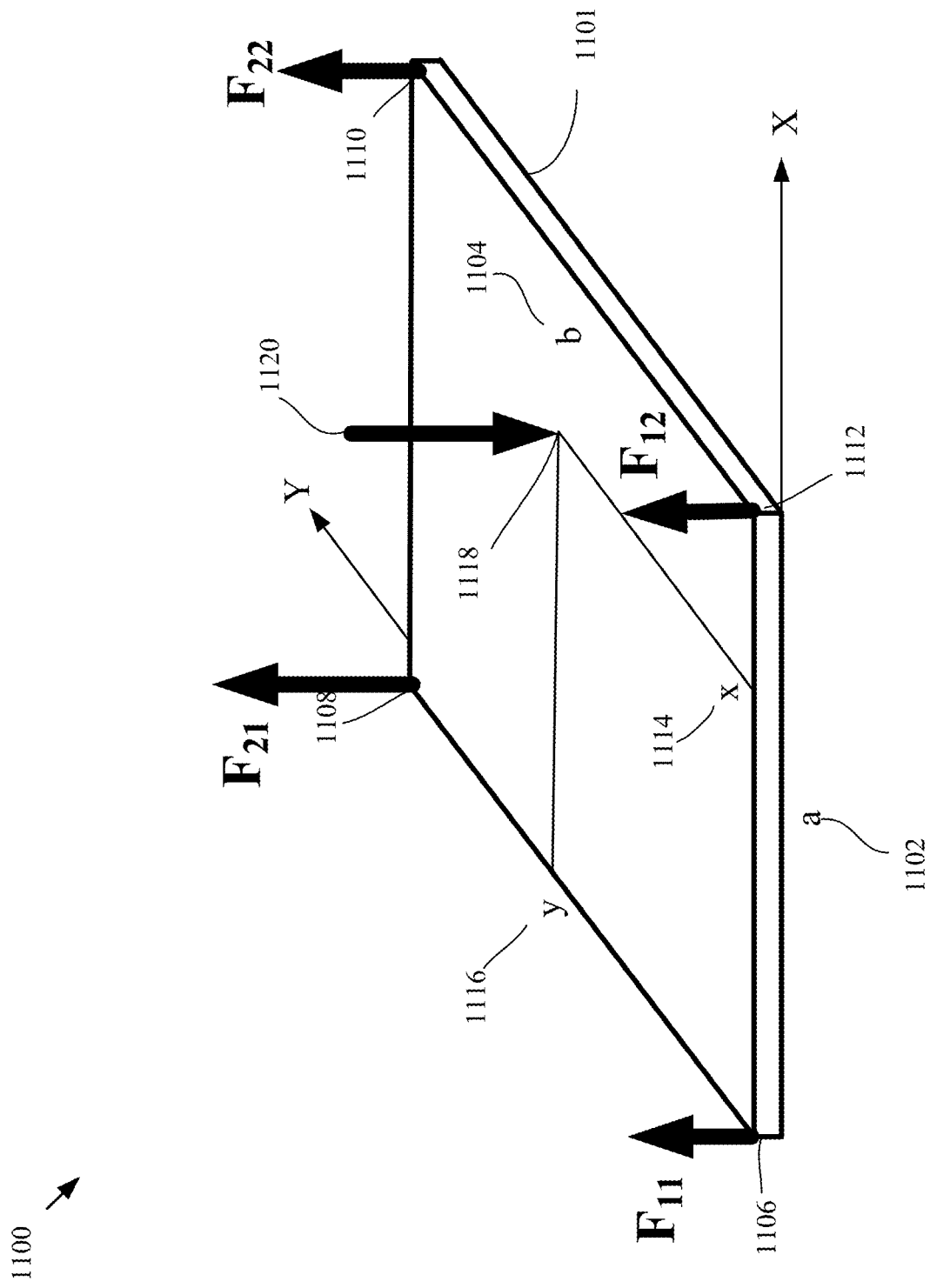
FIG. 11 depicts an example of force distribution in an illustrative implementation of an apparatus as described herein that uses four pressure sensors.

FIG. 11 depicts an example of force distribution 1100 in an illustrative implementation of an apparatus as described herein that uses four pressure sensors. FIG. 11 illustrates a sensing module 1101, such as the sensing module 1000 of FIG. 10. The sensing module 1101 has a width 1102 of size a millimeters and a length 1104 of size b millimeters. The length of the sensing module 1101 runs along the direction of the radial artery in the arm from the location 1106 toward the location 1108. That is, the locations 1108 and 1110 would be closer to the user's palm than the locations 1106 and 1112. FIG. 11 illustrates a reconstruction of the two-dimensional force distribution that the body (e.g., the skin over or about an artery) applies to the sensing module 1101.

In the sensing module 1101, four pressure sensors are used. Consequently, regardless of the exact placement of the sensing module 1101 proximal to an artery (e.g., the radial artery), at least one of the pressure sensors can detect (e.g., sense, measure, etc.) a good tonometry signal, or equivalently, a pulse signal. The sensing ability of the sensing module 1101 increases with the number of pressure sensors. That is, the more the pressure sensors, the higher the likelihood that at least one of the sensors will be placed over the skin for optimal signal detection.

The sensing module 1101 is illustrated as including four pressure sensors that are placed at respective corners of the sensing module 1101. The four pressure sensors are placed respectively close to locations 1106-1112 of the sensing module 1101. The directions of the arrows at the locations 1106-1112 indicate the direction of sensing. As mentioned above, more or less pressure sensors can be used. For example, two, three, or more pressure sensors can be used. In an example, the number of pressure sensors can be such that an epicenter 1118 of the forces applied by the flow of blood though the artery can be calculated. The epicenter 1118, and as further described below, corresponds to the 2D point on the sensing module at which the pulses through the artery are actually timed the most. The (x, y) coordinates of the epicenter and a total force 1120 (e.g., pressure) at the epicenter can be calculated using formula (1)

$$\begin{cases} F = F_{11} + F_{12} + F_{21} + F_{22} \\ x = a \times \dfrac{F_{12} + F_{22}}{F_{11} + F_{12} + F_{21} + F_{22}} \\ y = b \times \dfrac{F_{21} + F_{22}}{F_{11} + F_{12} + F_{21} + F_{22}} \end{cases} \quad (1)$$

In formula 1, the total force, F, at the epicenter 1118 is the sum of all the measured forces at each of the locations 1106-1112 of pressure sensing. The value x in formula (1) corresponds to the location 1114 of the x coordinate of the epicenter 1118. The value y in formula (1) corresponds to the location 1116 of the y coordinate of the epicenter 1118.

The calculated location of the epicenter 1118 can be used to detect whether, upon re-wearing of the wearable device, the location of the sensing module over the artery is changed compared to the last time(s) that the device was worn by the user and by how much. To restate, for example, upon wearing the wearable device on the wrist on a first day, the sensing module may be at a first location over the radial artery. On a second day, when the user re-wears the wearable device, as it unlikely that the sensing module is at the exact location as that of the first day. As such, by tracing the route of the pulse propagation (i.e., the movement of the epicenter), any techniques for determining blood pressure metrics can compensate for any changes in the route of the epicenter.

Several techniques can be used to estimate the blood pressure of a user using the pressure sensors of a sensing module.

A first technique for estimating the blood pressure using pressure sensors can include measuring a transition of a pulse wave pressure along a sensing module; and estimating the blood pressure using at least one of temporal properties or geometrical properties of the pulse wave.

Having more pressure sensors available in a sensing module provides a wider view of the blood flow in an artery than would be possible with fewer pressure sensors. Consequently, more information regarding the blood flow can be extracted from the relatively small sized stage (i.e., the sensing module, the lower module) as the blood flows against the sensing platform (i.e., the sensing module). Such blood flow information can be used to infer or derive the PWV. For example, the pressure pathway along the sensing module can be mapped using pressure information from the multiple pressure sensors. The blood flow velocity can then be estimated from the pressure pathway. Pressure pathway refers to the progressing of pressure (e.g., at the epicenter) along the sensing module.

The blood velocity and the blood pressure are correlative. For example, a higher blood pressure results in the higher blood velocity (e.g., speed) of the blood in the blood vessels. Similarly, higher blood velocity is indicative of higher blood pressure. However, as it difficult to directly measure the blood pressure, which is the pressure inside arteries, the swing effect of the pressure sensors can be used to estimate the blood velocity, and from the blood velocity, the blood pressure. The swing effect is so called because, as the pressure wave moves across the sensing module, the pressure sensors give way to (e.g., move, displace, swing, etc.) the part of the sensing module where they are placed. The swing effect can be used to estimate the different times (e.g., the delta times) that a pressure wave hits (e.g., arrives at) each pressure sensor. That is, the swing effect can be used to estimate the progress velocity of the pressure wave along the sensing module. To reiterate, by estimating (e.g., calculating) the blood velocity, the blood pressure inside the blood vessels can be estimated because the blood velocity and the blood pressure are correlated.

As the blood flows over the sensing module, mainly in the Y direction of the sensing module 1101, from the locations 1106, 1112 towards the locations 1108, 1110, the pulse wave of the blood so moves as well. As any other waves, the pulse waves front. How front points move over the Y and X directions of the sensing module can be tracked. In an example, the peek (i.e., maximal, strongest) front point can be tracked over time, where the time corresponds to heartbeat. With each heartbeat, the front point moves from the start to the end of the sensing module. The front point is indicated by the epicenter 1118 of FIG. 11. That is, the epicenter 1118 illustrates the instantaneous and maximal front point of the blood wave that is sensed (and tracked) by an apparatus according to this disclosure.

At each sampling time, the (x, y) location of the epicenter 1118 on the sensing module can be calculated from the pressure sensor measurements. For example, assuming a sampling frequency of 64 Hz (i.e., 64 samples per second), and a heartbeat of 60 beats-per-minute, then with every heartbeat, and using the formula (1), 64 locations of the epicenter 1118 and respective force values, can be calculated.

As mentioned above, the velocity of a blood wave as the blood wave passes under a sensing module is referred to herein as the PFV. The PFV can be calculated by measuring how the peak (i.e., the epicenter 1118) of a pulse travels along the sensing module. Even though the PFV is a measure of the pulse velocity along a small distance (i.e., the length 1104, b, of FIG. 11), PFV can be assumed to be correlated to, if not the same as, the PWV.

As is known, the relationship between PWV and the blood pressure can be derived using the Moens-Korteweg equation $$PWV = \sqrt{\frac{E_{inc} \times h}{2r\rho}},$$

where $E_{inc}$ is the elasticity modulus of the blood vessel, h is the thickness of the blood vessel, r is the radius of the blood vessel, and $\rho$ is the blood density. Using the Moens-Korteweg equation, a relationship between the PWV and the blood pressure can be derived as $P_s = b_1/PWT^2 + b_2$, wherein $P_s$ is the systolic blood pressure, PWT is the pulse wave transit time, $b_1$ and $b_2$ are coefficients derived using measured values of blood pressure of a user and measured values of PWT. PWT can be derived as PWT=distance/PWV. That is, the pulse wave transit time (PWT) is, for example, the distance from the heart to the wrist size divided by the pulse wave velocity.

As PWV is not known, PWT can be approximated by PWT=d/PFV. That is, PWT can be approximated as the size of the sensing module divided by the velocity of the pulse wave along the sensing module. In another example, PWV and PFV may be related by the equation $PWV \cong \delta_1 * \alpha_2^{PFV} + \alpha_3$ where $\alpha_1$, $\alpha_2$, and $\alpha_3$ are empirically derived constants.

A second technique for estimating the blood pressure using pressure sensors can include measuring, using the pressure sensors, an absolute pressure value of an arterial wall; and estimating the blood pressure from the absolute pressure value.

As mentioned above, pressure measurements from the pressure sensors of the lower module can be continuously or episodically received. The pressure measurements can be used to determine the blood pressure.

Several techniques can be available for deriving the blood pressure from the pressure measurements. Some of the techniques may be data-driven (e.g., based on machine learning) while other techniques may be based on mathematical relationship between pressure measurements and blood pressure.

For example, in the case of machine learning, a neural network may be trained to output blood pressure values from the pressure measurements. In the training phase, the expected outputs of the neural network are measured blood pressure values; and inputs can include pressure measurements (from each of the sensors and/or the pressure at the epicenter) and characteristics of sample subjects (i.e., users). The measured blood pressure values are blood pressure measurements of the sample subjects that are measured using traditional blood pressure measurement techniques and instruments (e.g., an ECG device, a sphygmomanometer, other Korotkov-sounds-based device or technique). The characteristics of the sample subjects can include age, gender, height, weight, life style (e.g., sedentary, mildly active, very active, etc.), medical history (e.g., known diseases, hereditary information, etc.), other characteristics, or any combination thereof.

(Algorithm 6) A third technique for estimating the blood pressure using pressure sensors can include measuring displacement of arterial walls using ultrasonic sensors; and transforming the displacement of the arterial walls into a blood pressure measurement.

While not specifically mentioned above, a lower module (i.e., a sensing module) according to this disclosure can include one or more ultrasonic sensors. Information from the ultrasonic sensors can be used to measure the displacement of arterial walls. The displacement of arterial walls can be transformed (e.g., converted to, etc.) blood pressure values using, as described above, data-driven techniques or other techniques that may be based on mathematical relationship between displacement of arterial walls and blood pressure.

While not specifically mentioned above, and as is known in the art, signals (e.g., sensor data) received from any of sensors of a sensing module may be pre-processed by a DSP pipeline. For example, the signals may be filtered, amplified, modulated, demodulated, or the like. Such DSP pre-processing can be performed before the sensor information is used (such as in data-driven or mathematical techniques) to derive the blood pressure.

Figure 12:
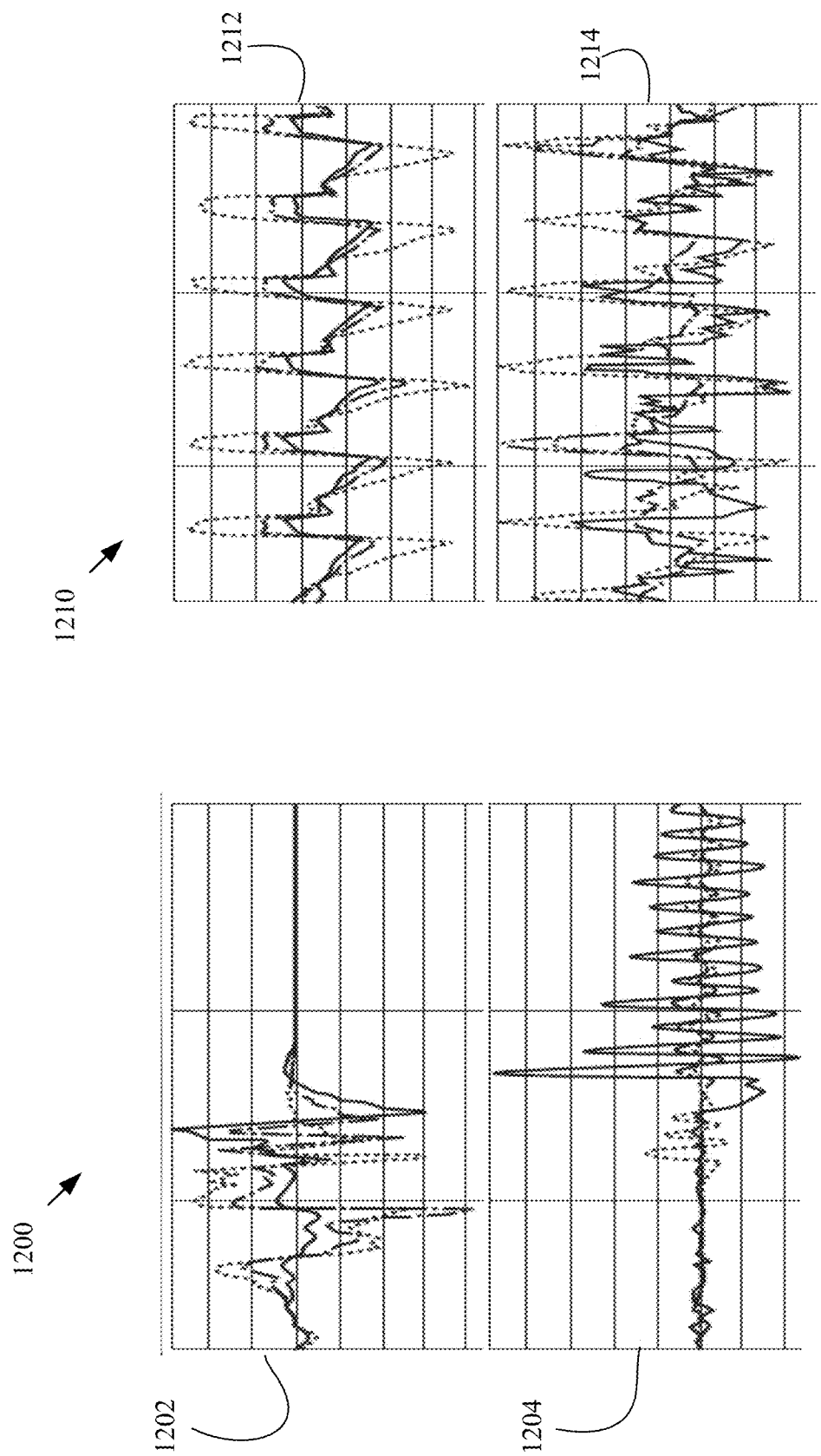
FIG. 12 illustrates examples of pre-processed and post-processed information received from sensors of a sensing device as described herein.

FIG. 12 illustrates examples of pre-processed and post-processed information received from sensors of a sensing device as described herein. Pre-processed signals 1200 illustrates an example of raw (e.g., pre-processed) signals as received from sensors of the sensing device. Post-processed signals 1210 illustrates an example of the pre-processed signals 1200 after processing through a DSP pipeline. A graph 1202 illustrates non-physiological signals as received from PPG sensors (e.g., photodiodes) of the sensing module; and a graph 1204 illustrates non-physiological signals as received from pressure sensors of the sensing module. A graph 1212, and a graph 1214 illustrate, respectively, post-processed signals showing four channels of PPG and four channels of pressure sensor of blood pulsation signals.

In some implementations of a wearable device according to this disclosure, a calibration process can be used to teach, correlate, or the like a measured (e.g., estimated) blood pressure to a true blood pressure value. The measured blood pressure is the blood pressure value as estimated by the wearable device from pressure sensor information. The true blood pressure is the blood pressure of the user as measured by a traditional device, such as ECG sensors and/or based on Korotkoff sounds. The calibration process may be performed once, daily, or at some other frequency. The calibration process provides an adjustment to the measured blood pressure values based on known, predictable, or expected changes and/or values.

A first calibration technique can include receiving the arterial blood pressure; calculating blood pressure metrics based on pressure sensor information; and generating a mapping between the arterial blood and calculated blood pressure metrics.

For example, upon initial wearing of a wearable device by a user, the user may be prompted to enter his/her blood pressure values (i.e., the arterial blood pressure). Alternatively, the wearable device may include an ECG sensor, and the user may be prompted to measure his/her blood pressure (i.e., the arterial blood pressure) using the ECG sensors. In yet another alternative, the arterial blood pressure may be received wirelessly from another device. For example, the other device can include an inflating and self-locking strap and can wirelessly transmit the blood pressure results to a connected device.

The wearable device may then estimate the user's blood pressure using pressure sensors of the wearable device, as described above. A mapping is then calculated between the measured blood pressure and the arterial blood pressure. To improve the accuracy of the mapping, the process may be repeated several times, at different times of the day, daily, and the like. From thereon, when a blood pressure value is estimated from pressure sensor information, the mapping is used to present to the user the arterial blood pressure based on the mapping. The mapping may be a linear or a non-linear mapping. The mapping can comprise mapping coefficients. The coefficients can be derived using a multiple regression with least squares approach.

In the calibration process described above, the user may be asked to remain in a still position while calculating blood pressure metrics based on pressure sensor information for the calibration process. In an alternative process, the user may be asked to change his/her body position for at least some of the blood pressure metrics to be calculated. For example, the user may be asked to stand, sit, elevate legs while sitting, and the like. The coefficients can be calculated while taking into account resting blood pressure values and the changes in the blood pressure due to the different body positions.

The calibration process can also be based on known hydrostatic effects. For example, it is known that elevation of a wrist above the head decreases the local blood pressure in the wrist by approximately +0.7 mmHg (for systolic pressure) and −0.5 mmHg (for diastolic pressure) for each cm the wrist is above heart level.

As such, during the measurement of the blood pressure metrics, the user can be prompted to change the position of his/her arm in such a way as to change the local blood pressure at the point of measurement. Based on the expected change in the measured values, the coefficients can be adjusted. For example, if the location of the wrist with respect to the heart is known (because, for example, the user was prompted to raise and/or lower his/her arm) at the time of measurement, the change in measured blood pressure at the different locations, as compared to the expected blood pressure values, can be used to adjust the coefficients. For example, whereas the expected change is −10 mmHg, but the measured change is 15 mmHg, the coefficients of the mapping can be adjusted to map the observed change of 15 mmHg to the expected −10 mmHg.

To account for anatomical differences between users, the user may be prompted to measure and provide to the wearable device the distances between the heart and the body part where the wearable device located prior to taking a measurement. In another example, the wearable device may include sensors from which the barometric pressure can be determined. As such, the change in barometric pressure can be used to determine the vertical distance of the sensing module to the heart.

A second calibration technique can include receiving arterial blood pressure values; selecting a model for the user using characteristics of the user; determining blood pressure metrics based on pressure sensor information; and using the model to map blood pressure metrics to an arterial blood pressure value.

That is, a wearable device may incorporate, such as in a database, several models. Each model may represent a mapping from measured blood pressure metrics using pressure sensors to arterial blood pressure values (as measured by traditional blood pressure techniques). Each model is based on characteristics of subject users. The characteristics can be as described above. To reiterate, anthropological properties and/or health conditions of the user can be used to select a model from amongst the available models. The model that results in the best match between the user's characteristics and match between measured blood pressure metrics and arterial blood pressure values is the model that is selected for the user. The selected model for the user can be used, whenever blood pressure of the user is to be measured, to translate (e.g., map) the measured blood pressure metrics to arterial blood pressure values.

A third calibration technique can include using waves of respiration for calibration. This technique is based on the known fact that there is a drift in blood pressure during respiration. The drift is in the range of 5 millimeters of mercury (mmHg). As such, the blood pressure measured with a wearable device according to this disclosure can be adjusted based on a detected wave of respiration. That is, the model coefficients, which are described above, can be derived by using the 5 mmHg drift into account. The rate of respiration and waves of respiration can be extracted from PPG sensors and from the blood pressure since it is known that the pulse changes during respiration. For example, during the inhaling cycle, the rate of the pulse slows down; and the opposite takes place during the exhaling cycle. As such, the pulse is continuously accelerating and decelerating. The respiration rates can be derived using spectral analysis of sensor information or from sensors that are dedicated for measuring respiration rates.

In a fourth calibration technique, arterial blood pressure is measured using a traditional measuring technique (such as one based on Korotkoff sounds); and blood pressure metrics are calculated based on pressure sensor information. A group of people with the most similar metrics can be formed and used to assesses the blood pressure metrics to transform (e.g., map) the blood pressure metrics into the arterial blood pressure. That is, as compared to the calibration technique described above where a model is selected from a set of available models, the instant calibration technique builds a model based on the most similar subjects in a database. That is, the most similar subjects (for example, based on selected characteristics) in a database are selected and the model is built using the selected subjects.

While the above calibration techniques may be listed as separate techniques, it is to be understood that at least some aspects of the techniques can be combined.

For example, known/expected changes due to barometric pressure changes (e.g., changing of the wrist position with respect to the heart) can be combined with known/expected changes due the respiratory cycle. That is, the calibration process described above with respect to the changing of the arm position can be augmented with measurements of respiration wave range in blood pressure at different arm positions. The respiration wave range at different arm positions taking into account the arm level with respect to the heart can be used to calculate the coefficients for a model and to determine the arterial blood pressure.

Figure 13:
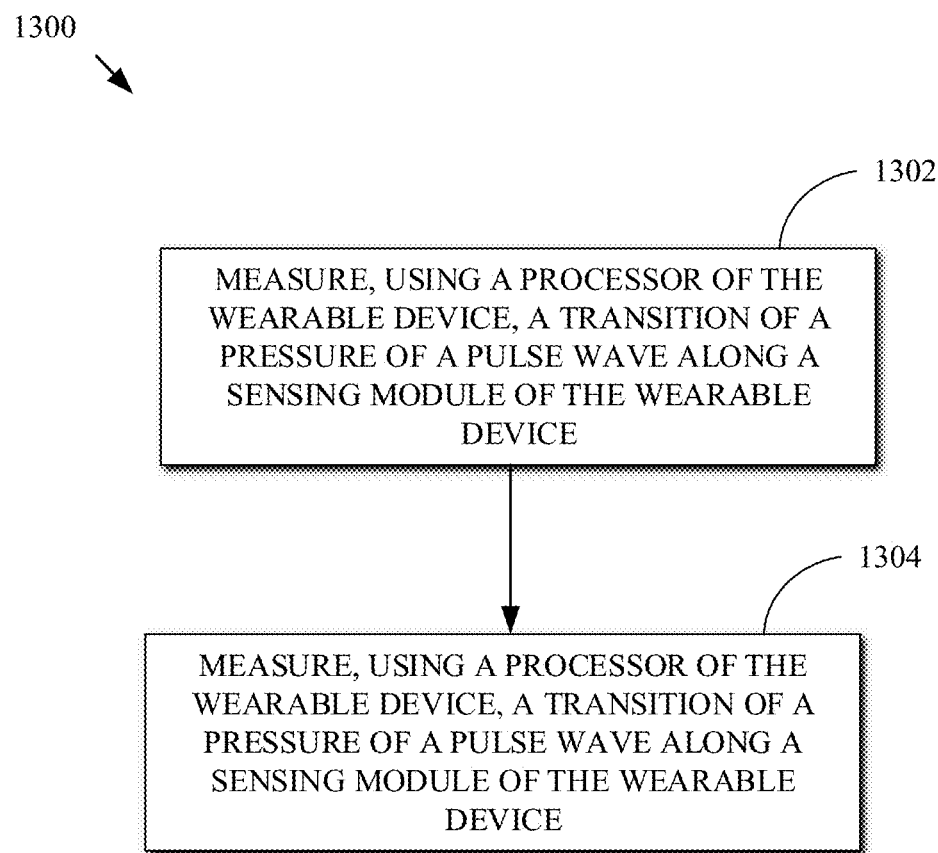
FIG. 13 is a flowchart of an example of a technique for measuring blood pressure according to an implementation of this disclosure.

FIG. 13 is a flowchart of an example of a technique 1300 for measuring blood pressure according to an implementation of this disclosure. The technique 1300 can be implemented by a wearable device that is worn by a user, such as the apparatus 100 of FIG. 1 or the apparatus 900 of FIG. 9. The technique 1300 can be implemented as executable instructions that can be stored in a memory, such as one of the storage system 830 or the ROM 820 of FIG. 8. The instructions can be executed by a processor, such as the processor 805 of FIG. 8, to perform the steps of the technique 1300. The technique 1300 can be implemented using specialized hardware or firmware.

At 1302, the technique 1300 measures, using a processor of the wearable device, a transition of a pressure of a pulse wave along a sensing module of the wearable device, as described above. At 1304, the technique 1300 estimates the blood pressure using at least one of temporal properties or geometrical properties of the pulse wave, as described above.

In an example, measuring, using the processor of the wearable device, the transition of a pulse wave pressure along the sensing module of the wearable device can include determining respective epicenter locations of pressure along the sensing module at respective sampling times, as described above with respect to FIG. 11. In an example, estimating the blood pressure using at least one of the temporal properties or the geometrical properties of the pulse wave can include, as described above, calculating, using the respective epicenter locations, a pulse front velocity (PFV), wherein the PFV being a velocity of a blood wave as the blood wave passes under the sensing module; estimating a pulse wave velocity (PWV) using the PFV; and estimating the blood pressure using the PWV.

In an example, estimating the pulse wave velocity (PWV) using the PFV can include, as described above, calculating a pulse wave transit time (PWT) as a longitudinal size of the sensing module divided by the PFV; and calculating the PWV as a distance from a heart of the user to a location of the sensing module divided by the PWT.

In an example, determining the respective epicenter locations of the pressure along the sensing module at the respective sampling times can include, as described above, determining, at a sampling time, respective pressure values at a plurality of pressure sensors of the sensing module, wherein the plurality of pressure sensors comprising at least two pressure sensors; and calculating a respective epicenter location using the respective pressure values. In an example, the PWV can be estimated from the PFV using a function $\alpha_1 * \alpha_2^{PFV} + \alpha_3$, wherein $\alpha_1$, $\alpha_2$, and $\alpha_3$ being constants, as described above.

In an example, the technique 1300 can further include receiving a calibration value; using the calibration value to create a mapping from estimated blood pressures to arterial blood pressures of the user; and adjusting the estimated blood pressure using the calibration value.

In an example, and as described above, receiving the calibration value can include receiving a first arterial blood pressure measurement based on a wrist of the user being at a first position, and receiving a second arterial blood pressure measurement based on the wrist of the user being at a second position; and using the calibration value to create the mapping can include creating the mapping based a difference between the first arterial blood pressure measurement and the first arterial blood pressure measurement and on a known hydrostatic difference of the wrist being at the first position and the second position. In an example, a known drift in blood pressure during respiration is used to derive the calibration value, as described above.

As mentioned above, some aspects of the disclosed implementations relate to predicting, using a machine-learning model, a predicted value where the ML model was trained using imbalanced data. Given an initial measurement of a prediction value (e.g., a baseline value, which can be a baseline blood pressure), the ML model can be used to predict (e.g., estimate) the prediction value at a current time (e.g., in a current time window). In an example, the ML model can estimate a difference between (e.g., the change between) the initial value and the prediction value in a current time window.

The techniques can be summarized by the steps: 1) using at least some (e.g., all) the paths from a window i (e.g., a baseline window, an initial window) to a current window j (e.g., a prediction window, an assessment window) to obtain a respective estimate of the prediction value for each of the paths, and 2) combining the respective estimates of the prediction value to obtain a final estimate of the prediction value. Any number of methods can be available for analyzing the distribution of the results (i.e., the respective estimates of the prediction value) and estimate the difference between the window i and the window j. The analysis of the distribution of the results can be used to obtain weights for combining the respective estimates of the prediction value.

A path can be thought of a set of data hops (e.g., time hops) from the window i to the window j. Equation (2) illustrates all of the k paths from the window i to the window j.

$$\begin{cases} \theta_{i,j}^0 = \theta_{i,j} \\ \theta_{i,j}^1 = \theta_{i,j-1} + \theta_{j-1,j} \\ \theta_{i,j}^2 = \theta_{i,j-2} + \theta_{j-2,j-1} + \theta_{j-1,j} \\ \theta_{i,j}^3 = \theta_{i,j-3} + \theta_{j-3,j-2} + \theta_{j-2,j-1} + \theta_{j-1,j} \\ \theta_{i,j}^4 = \theta_{i,j-4} + \theta_{j-4,j-3} + \theta_{j-3,j-2} + \theta_{j-2,j-1} + \theta_{j-1,j} \\ \vdots \\ \theta_{i,j}^K = \theta_{i,i+1} + \theta_{i+1,j} \end{cases} \quad (2)$$

Figure 14:
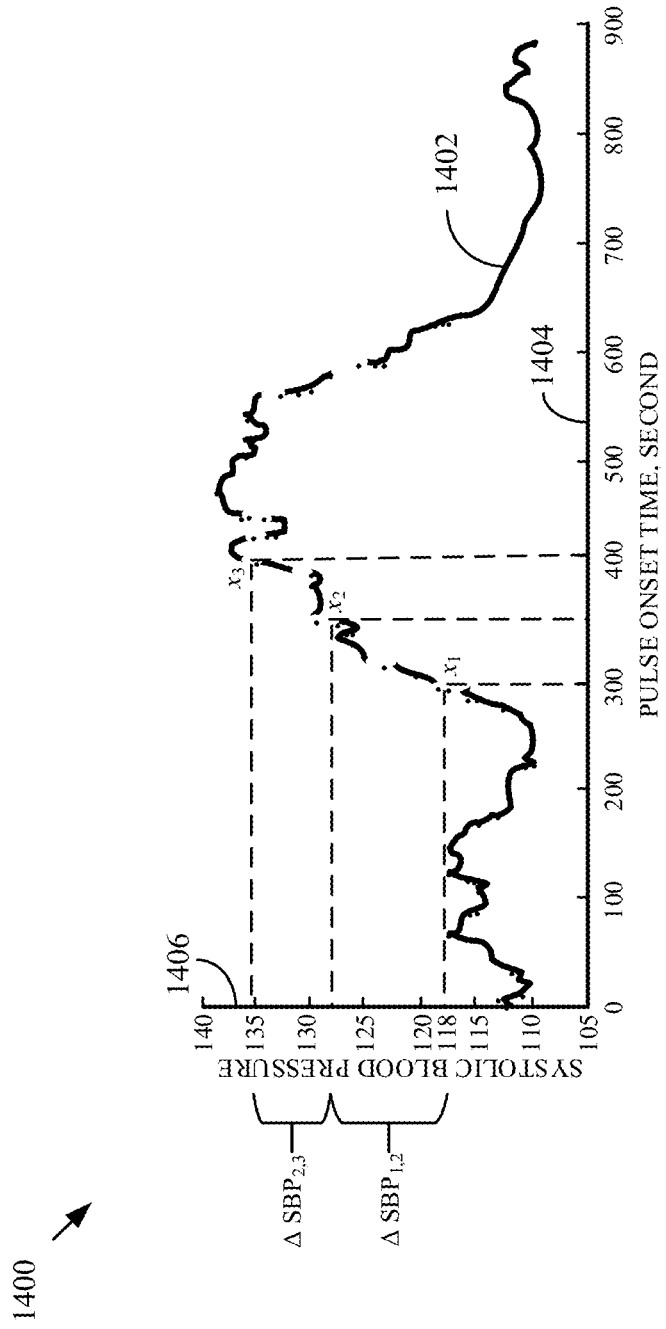
FIG. 14 illustrates an example of paths between two windows according to implementations of this disclosure.

FIG. 14 illustrates an example 1400 of paths between two windows according to implementations of this disclosure. FIG. 14 shows systolic blood pressure over time. The blood flow can be segmented into individual pulses, where each pulse corresponds to a heartbeat. The starting point of each pulse is referred to as the pulse onset time. Each pulse has a systolic and a diastolic blood pressure value. However, for simplicity of explanation, FIG. 14 only shows the systolic value. A graph 1402 shows the measured systolic blood pressure for each pulse over a 900-second period. Each point on the graph indicates one pulse. An x-axis 1404 shows the start time of the pulse, and a y-axis 1406 shows the systolic blood pressure of the pulse. The graph 1402 can be read as follows: For the pulse that started at 300 seconds after recording, the blood pressure is 118 mmHg.

To measure the systolic blood pressure changes $\Delta SBP_{31}$ from point $x_1$ to point $x_3$, a trained ML model that is as described herein can be used to predict each of $\Delta SBP_{31}^0$, $\Delta SBP_{32}$, and $\Delta SBP_{21}$, and then combine these predictions, as a weighted sum, to obtain $\Delta SBP_{31}$. The weights can be calculated (e.g., determined, etc.) based on the training data. $\Delta SBP_{31}^0$ is the prediction obtained from the ML model of a blood pressure change between $x_3$ and $x_1$.

The trained ML model can be used to predict changes in blood pressure, such as throughout the day. The ML model can be included in a wearable device that is worn by the user. The wearable device uses sensor data to estimate, using the ML model, changes in the user's blood pressure throughout the day. Alternatively, the ML model can be included in another device that is in communication with the wearable device and that receives the sensor data from the wearable. The sensor data can be used to extract features that can be used to obtain the inputs to the ML model. At a given time point, the features to be input to the ML model can be an average (or some other combination) of a set of features that are collected in a window of time. The features extracted can be, can include, or can be derived from the features described with respect to FIGS. 6A-6C, FIG. 7, or FIG. 12.

To illustrate, assume that $x_1$ ($x_1$=118) of the example 1400 is an initial blood pressure of the user. The initial blood pressure can be a baseline blood pressure that is measured using, for example, an ECG sensor. In an example, the wearable device itself can include the ECG sensor. As described above, features differences can be input to the ML model to obtain an estimated change in blood pressure. The estimated change in blood pressure can be added to the initial blood pressure to obtain the final blood pressure. The wearable device can provide messages to the user based on the value of the final blood pressure. For example, if the estimated blood pressure is high, a warning message can be provided to the user. The message can be an audible, visual, textual, haptic, other type of message, or a combination thereof.

The example 1400 illustrates that there are two ways to estimate the blood pressure change, $\Delta SB_{1,3}$, between an initial measurement $x_1$ and a current estimate $x_3$.

A such, instead of only predicting the large change between $x_3$ and $x_1$ (i.e., $\Delta SBP_{1,3}$), the change can also be predicted in smaller steps using ranges (i.e., $x_1$ to $x_2$, or $\Delta SBP_{1,2}$, and $x_2$ to $x_3$, or $\Delta SBP_{2,3}$). This prediction can be combined with the prediction derived as the change from $x_1$ and $x_3$ ($\Delta SBP_{1,3}$) to obtain a final prediction: $\Delta SB_{1,3}$ can be estimated directly, or it can be estimated as a combination of estimated $\Delta SBP_{2,3}$ and $\Delta SBP_{1,2}$ values. A combination of these two ways can result in a more accurate estimation of $\Delta SBP_{1,3}$. The different ways can result in a series of estimations for a point. This series can have a specific distribution, as further described below.

Figure 15:
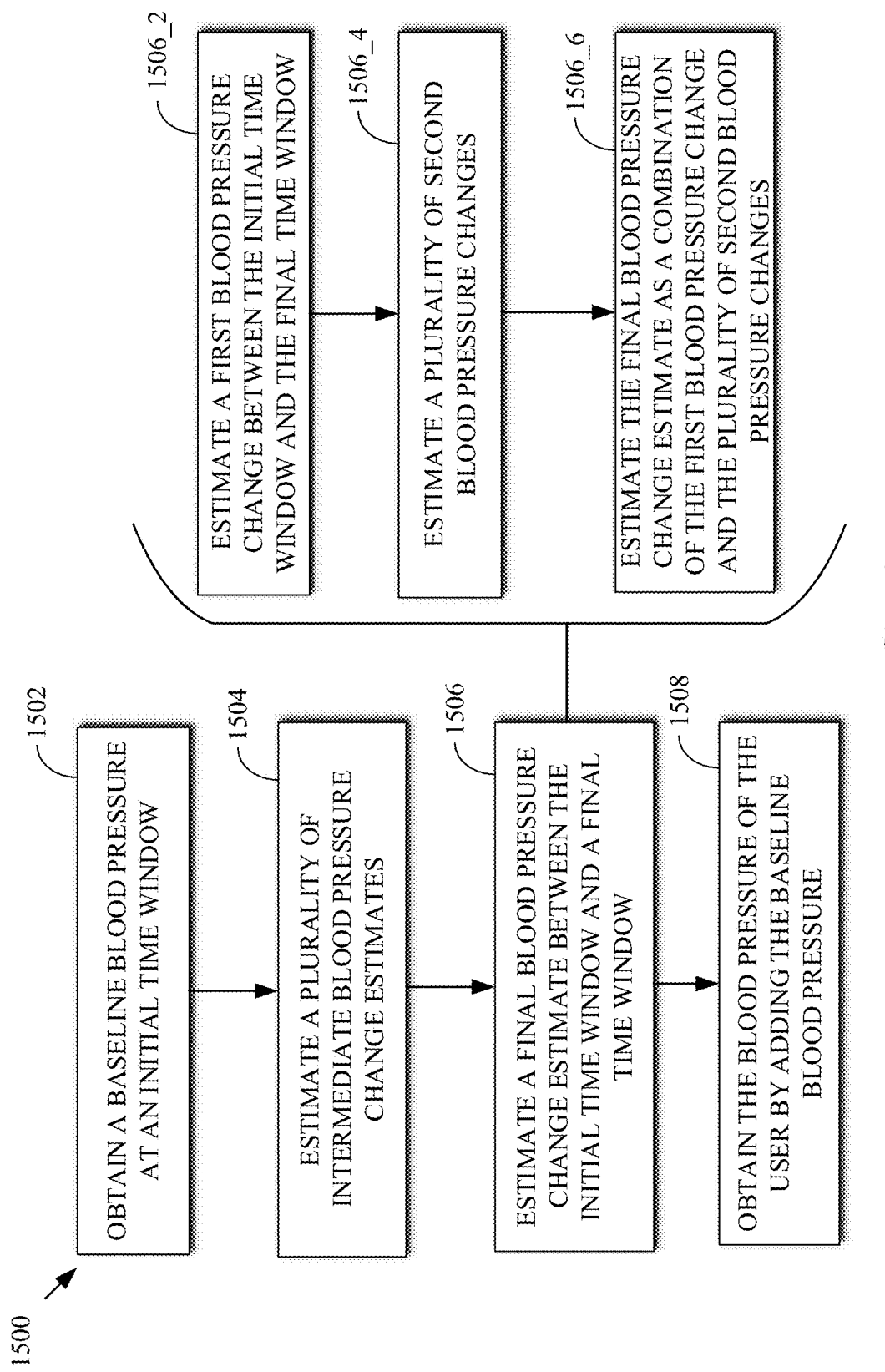
FIG. 15 is an example of a technique for estimating a blood pressure of a user according to implementations of this disclosure.

FIG. 15 is an example of a technique 1500 for estimating a blood pressure of a user according to implementations of this disclosure. The technique 1500 can be implemented by a wearable device, such as the apparatus 100 of FIG. 1 or the apparatus 900 of FIG. 9, or some other wearable device that includes sensors. The sensors can include PPG sensors, a sensing module (such as the sensing module 1000 of FIG. 10), optical sensors, light sensors, pressure sensors, more sensors, fewer sensors, other sensors, or a combination thereof. The technique 1500 can be implemented, for example, as a software program that may be executed by a processor-based computing system, such as the system 800 of FIG. 8. In an example, the processor-based computing system can be device separate from the wearable device and is in communication with the wearable device to receive sensor data, display messages on the wearable device, and the like. The software program can include machine-readable instructions that may be stored in a memory such as the RAM 810 or the ROM 820 of FIG. 8, or a secondary storage, such as the storage system 830 of FIG. 8, and that, when executed by a processor, such as the processor 805, can cause the processor-based computing system to perform the technique 1500.

The technique 1500 estimates (e.g., predicts) a change in blood pressure between a first time (e.g., an initial time window) and a current time (e.g., a final time window). The technique 1500 obtains several estimates of the change in the blood pressure and combines the several estimates to obtain a final blood pressure change estimate, as described above. Each of the several estimates of the change in the blood pressure is obtained using a unique data path (or equivalently, time path) from the initial time window to the final time window.

To estimate the change in blood pressure between a first time window and a second time window, the technique 1500 obtains, at the first time window, first features based on sensors of a wearable device; obtains, at the second time window, second features based on the sensors of the wearable device of the user; obtains respective feature differences between the first features and the second features; and uses the respective feature differences as input to a ML model to obtain the first blood pressure change.

As mentioned above, the ML model can be trained to receive predictive feature differences and output an estimated blood pressure difference. The ML model can also receive as input the feature values from the initial window and the feature values from the current window. For illustration purposes only, assume that two features ($F_1$ and $F_2$) are extracted from the sensor data to be used for estimating the blood pressure change. Thus, the first features at the first time window can be $F_1^{t=1}$ and $F_2^{t=1}$; the second features at the second time window can be $F_1^{t=2}$ and $F_2^{t=2}$; and the features differences can be $(F_1^{t=2}-F_1^{t=1})$ and $(F_2^{t=2}-F_2^{t=1})$. These features differences (and, in some examples, $F_1^{t=2}$ and $F_2^{t=2}$ and $F_1^{t=1}$ and $F_2^{t=1}$) can be used as inputs to the ML model. As can be appreciated, many predictive features are possible. The term "feature differences," as used herein, is not limited to subtraction of the respective feature values. Rather "feature differences" encompasses other ways of combining the features, other than subtraction. For example, ratios (e.g., $F_1^{t=2}/F_2^{t=2}$ and $F_1^{t=2}/F_1^{t=1}$) of the respective feature values, logarithmic functions of the respective features, or other functions (or feature manipulations) of the respective features can be used. For example, the log transform from the first window (e.g., $\log(F_1^{t=1})$, $\log(F_2^{t=1})$) can be used. For example, differences between two features scaled by the first window's systolic blood pressure measurement $$\left(\text{e.g., } \frac{F_1^{t=2} - F_1^{t=1}}{SBP^{t=1}}\right)$$

can be used. For example, differences between two features scaled by the first window's diastolic blood pressure measurement $$\left(\text{e.g., } \frac{F_1^{t=2} - F_1^{t=1}}{DBP^{t=1}}\right)$$

can be used.

The features can include one or more of a pulse transit time, an amount of pressure that blood exerts on a skin surface of the user, a pulse front velocity, a pulse onset time, more features, fewer features, other features, or a combination thereof. For example, the wearable device can include sensors for measuring blood flow, the pressure that the blood exerts on the veins and on the skin surface of the user, velocity of the blood flow, amplitude of the pulse of the user, amplitude of PPG signals, and so on. The features can also include personal features to the user, such as age, gender, body type, weight, height, more, fewer, other personal features, or a combination thereof. Features differences are calculated for at least some of the features extracted from sensor data. However, personal features can be used as is. As mentioned, the features can be used to determine changes in blood pressure between two time windows.

The technique 1500 is discussed with respect to blood pressures (or features) in time windows. However, as used herein, the term "time window" also encompasses a "time point." In an example, the features in a time window may be features extracted based on one sampling of the sensors. In another example, several samples of sensor data can be obtained in the time window and the features can be extracted from the several samples. For example, the several samples can be averaged.

At 1502, the technique 1500 obtains a baseline blood pressure at an initial time window. In an example, the baseline blood pressure can be obtained by measuring the baseline blood pressure. As mentioned above, the initial blood pressure can be measured using a traditional blood pressure measurement technique and/or instrument. For example, the baseline blood pressure can be obtained during a calibration phase of the wearable device or some other time (e.g., once per week, one per day, etc.).

In another example, the baseline blood pressure can be a blood pressure that is an estimated blood pressure. As mentioned above, and further explained below, different data paths (e.g., ways) from the initial time window to a current window are used to estimate a change in blood pressure between the initial time window and the final time window. That is, several estimates of the change in the blood pressure are obtained and combined. In some implementations, the number of estimates of the change in the blood pressure may be limited to a maximum number (e.g., 10, 15, or some other lower or higher number). In an example, a subset of the total possible paths is selected for obtaining the several estimates of the change in the blood pressure such that the size of the subset is equal to the maximum number. In another example, the baseline blood pressure can be a previously estimated blood pressure selected such that the total number of paths from the initial time window to the final time window does not exceed the maximum number. Other ways of selecting the initial blood pressure are possible.

At 1504, the technique 1500 estimates a plurality of intermediate blood pressure change estimates. The intermediate blood pressure change estimates correspond to respective time windows that are subsequent to the initial time window. For example, assuming that the initial time window is $t_i$ and the final time window is $t_j$, then the technique 1500 obtains intermediate blood pressure change estimates for the time windows $t_{i+1}, t_{i+2}, \ldots, t_{j-2}, t_{j-1}$.

At 1506, the technique 1500 estimates a final blood pressure change estimate between the initial time window and a final time window. Estimating the final blood pressure can be as described with respect to 1506_2-1506_6.

At 1506_2, the technique 1500 estimates a first blood pressure change between the initial time window and the final time window. That is, features differences between the initial time window (e.g., the first time window as described above) and the final time window (e.g., the second time window as described above) can be used to obtain, from the ML model, a direct estimate of the change in blood pressure (i.e., the first blood pressure change).

At 1506_4, the technique 1500 estimates a plurality of second blood pressure changes. Each second blood pressure change is between a respective time window of the respective time windows and the final time window. For example, the second blood pressure changes can be, respectively, the changes from the time window $t_i$ to each of the time windows $t_{i+1}, \ldots, t_{j-1}$.

At 1506_6, the technique 1500 estimates the final blood pressure change estimate as a combination of the first blood pressure change and the plurality of second blood pressure changes. Any number of ways of combining the first blood pressure change and the plurality of second blood pressure changes can be available. In an example, the final blood pressure change estimate can be calculated as an average of the first blood pressure change and the plurality of second blood pressure changes. In another example, the final blood pressure change estimate can be calculated as a weighted average.

For example, the weights assigned to the first blood pressure change and each of the plurality of second blood pressure changes can be based on the training data. For example, a given blood pressure change can be assigned a weight that is equivalent to frequency of that given blood pressure change in the training data. That is, the weight of the given blood pressure change can be equal to the number of occurrences of the given blood pressure change divided by the total number of data samples in the training data. In another example, the weights can be based on clustering, as further described below.

At 1508, the technique 1500 obtains the blood pressure of the user by adding the baseline blood pressure to the final blood pressure change estimate.

Figure 16:
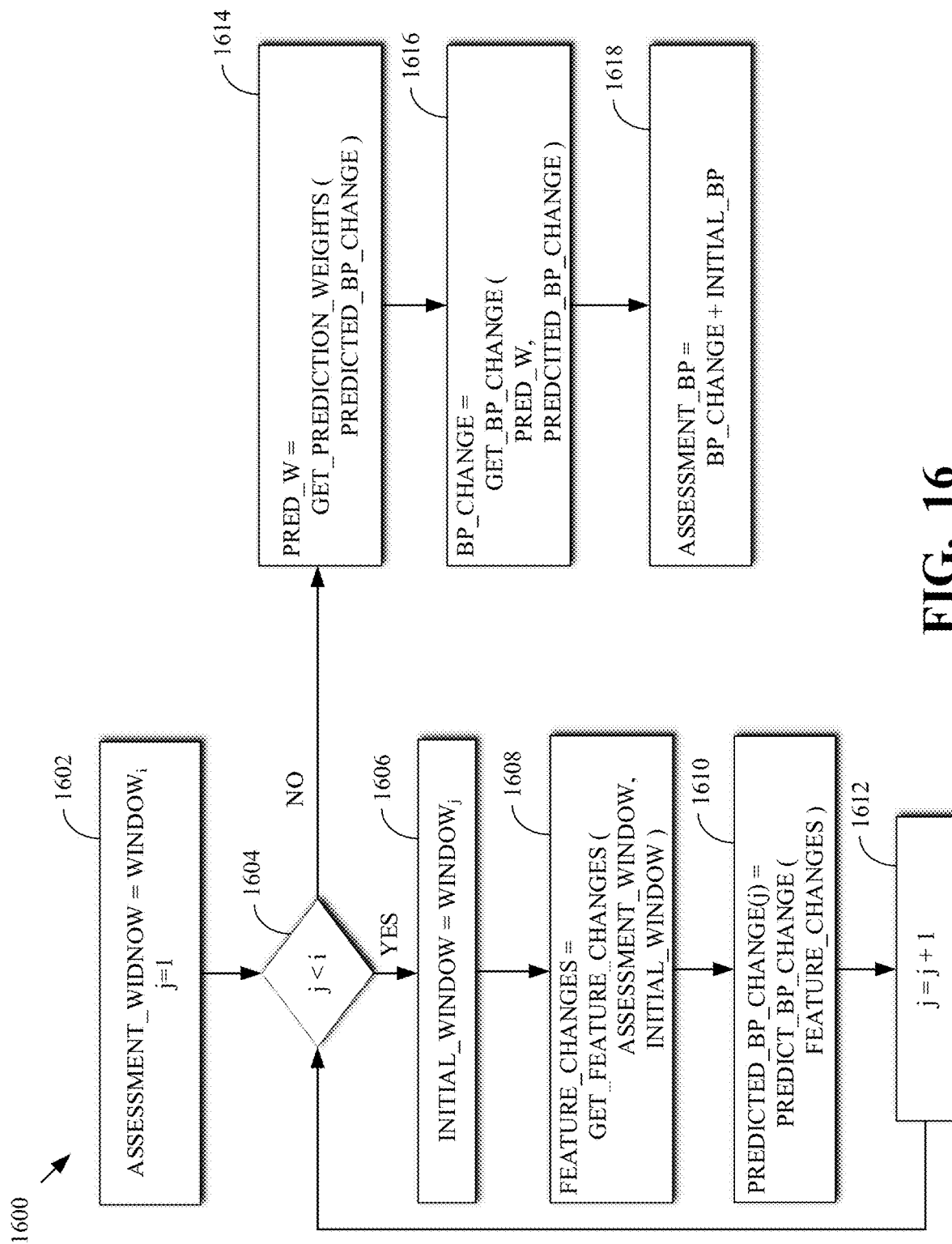
FIG. 16 is an example of a technique that can be used by the technique of FIG. 15.

FIG. 16 is an example of a technique 1600 that can be used by the technique of FIG. 15. An initial time window is $WINDOW_1$ and a current (e.g., final) time window is $WINDOW_i$. The technique 1600 can be used to estimate a blood pressure in $WINDOW_i$ given an initial blood pressure in $WINDOW_1$.

To describe the steps of the technique 1600, assume that an initial blood pressure measurement was taken at 9:00 AM in the morning, that the wearable device estimates the change in blood pressure every hour, and that it is now 1:00 PM. Thus, the wearable device has already estimated the change in blood pressure at 10:00 AM, 11:00 AM, and 12:00 PM. Thus, $WINDOW_1$ corresponds to the measurement at 9:00 AM and $WINDOW_i$ corresponds to the estimated change in blood pressure at 1:00 PM and, in this example, i=5. It is noted that, as mentioned above, the initial blood pressure measurement need not be a measured blood pressure. Rather, and as described above with respect to the maximum number of estimates to be combined, the initial blood pressure can be an estimated blood pressure.

At 1602, the technique 1600 initializes an ASSESSMENT_WINDOW variable to be the time window for which the blood pressure difference is to be calculated and initializes a loop variable j to 1. Thus, the ASSESSMENT_WINDOW is set to the time window corresponding to 1:00 PM. The variable j is used for each of the time windows between the initial time window (e.g., at 9:00 AM) to the current time window (at 1:00 PM), including the initial time window but excluding the current time window. Thus, the variable j will take on the values 1-4.

At 1604, the technique 1600 tests whether j is less than i. That is, the technique 1600 determines whether a predicted blood pressure change between a previous time window and the current window has not yet been estimated. If so (i.e., if j<i), then the technique 1600 proceeds to 1606; otherwise the technique 1600 proceeds to 1614.

At 1606, the technique 1600 assigns a variable INITIAL_WINDOW to $WINDOW_j$. Thus, when j is 1, 2, 3, and 4, INITIAL_WINDOW is set, respectively, to the window corresponding to 9:00 AM, 10:00 AM, 11:00 AM, and 12:00 PM.

At 1608, the technique 1600 calculates the feature changes, FEATURE_CHANGES, between the ASSESSMENT_WINDOW (e.g., 1:00 PM) and the INITIAL_WINDOW. The variable FEATURE_CHANGES can be an array, a vector, a bag, or some other data structure. Thus, when j=1, 2, 3, and 4, FEATURE_CHANGES includes the feature differences between first features of the time window corresponding to 1:00 PM and the second features of the time windows corresponding, respectively, to 9:00 AM, 10:00 AM, 11:00 AM, and 12:00 PM. A function GET_FEATURE_CHANGES receives as input the ASSESSMENT_WINDOW and INITIAL_WINDOW time windows and returns the feature differences. While not specifically shown, the function GET_FEATURE_CHANGES can have access to, or can extract, the features collected (e.g., extracted, etc.) from sensor data of the wearable device at the different time windows.

At 1610, the technique 1600 obtains a predicted blood pressure change, PREDICTED_BP_CHANGE, given the feature changes obtained at 1608. The technique 1600 is shown as using a function PREDICT_BP_CHANGE that returns the predicted change in blood pressure when certain changes in features are used as input. The function PREDICTED_BP_CHANGE can use the ML model to obtain the predicted blood pressure change.

At 1612, the loop variable j is incremented and control is returned to 1604. When the loop exists (i.e., when j=i), the data structure PREDICTED_BP_CHANGE contains at locations 1, 2, 3, and 4, the blood pressure changes between the window corresponding to 1:00 PM and, respectively, the windows corresponding to 9:00 AM, 10:00 AM, 11:00 AM, and 12:00 PM. Thus, PREDICTED_BP_CHANGE(1) corresponds to the first blood pressure change between the initial time window and the final time window that is estimated at 1506_2 of FIG. 15; and PREDICTED_BP_CHANGE(2) to PREDICTED_BP_CHANGE(4) correspond to the plurality of second blood pressure changes that are estimated at 1506_4 of FIG. 15.

At 1614, the technique 1600 obtains a set of weights PRED_W where each weight PRED_W(k) corresponds to a predicted blood pressure PREDICTED_BP_CHANGE(k). The weights can be obtained using a function GET_PREDICTION_WEIGHTS. In an example, the weights can be obtained based on clustering of the training data, as further explained below.

At 1616, the final blood pressure change, BP_CHANGE, can be obtained. A function GET_BP_CHANGE can be used to calculate the final blood pressure change. The predicted blood pressure PREDICTED_BP_CHANGE(k), calculated at 1610, and the weights PRED_W, calculated at 1614, are used as inputs to the function GET_BP_CHANGE.

The function GET_BP_CHANGE can calculate the final blood pressure change using calculations similar to those described with respect to equation (2) and using different paths (including data hops) from the initial time window to the final time window. That is, the technique 1600 calculates a plurality of blood pressure change estimates where each estimate corresponds to a different data path (e.g. data hop, time hop) from the initial time window to the final time window. For example, a respective prediction of the blood pressure change can be estimates for each of the paths (1 5), (1 4)(4 5), (1 3)(3 5), (1 3)(3 4)(4 5), (1 2)(2 5), (1 2)(2 4)(4 5), (1 2)(2 3)(3 5), and (1 2)(2 3)(3 4)(4 5). In the previous sentence a tuple (X Y) is to be read as "a blood pressure change between ($WINDOW_x$ and $WINDOW_y$). As such (4 5) means "the blood pressure change from the 12:00 PM measurement to the 1:00 PM measurement", (2 4) means "the blood pressure change from the 10:00 AM measurement to the 12:00 PM measurement," and so on.

Using equation (2), $\theta_{i,j}$ can be the blood pressure change between 9:00 AM and 1:00 PM. Thus, $\theta_{i,j}^1$ can be the change from 9:00 to 12:00 PM ($\theta_{i,j-1}$) plus the change from 12:00 PM to 1:00 PM ($\theta_{j-1,j}$); $\theta_{i,j}^2$ can be the change from 9:00 AM to 11:00 AM ($\theta_{i,j-2}$) plus the change from 11:00 AM to 12:00 PM ($\theta_{j-2,j-1}$) plus the change from 12:00 PM to 1:00 PM ($\theta_{j-1,j}$); and so on.

It is noted that, while the technique 1600, as explained above, does not calculate some of (X Y) hops, these are understood to have been calculated in previous invocations of the technique 1600, such as, for example, when calculating a final blood pressure change between 9:00 and 11:00 or a final blood pressure change between 9:00 and 12:00 PM. Thus, the GET_BP_CHANGE would have access to such previously calculated blood pressure changes and their corresponding weights.

Assuming that a total number of K+1 blood pressure changes (i.e., $\theta_{i,j}^{k=0...K}$) with respective weights $w^{k=0...K}$, then the technique 1600 can calculate BP_CHANGE using equation (3).

$$BP\_CHANGE = \frac{\Sigma_{k=0...K} w^k \cdot \theta_{i,j}^k}{\Sigma_{k=0...K} w^k} \quad (3)$$

Thus, the final blood pressure change estimate can be estimated as a weighted combination of the first blood pressure change and the plurality of second blood pressure changes, as described with respect to equation (3).

At 1618, the technique 1618 can obtain the final blood pressure value for the $WINDOW_j$ (e.g., an estimate of the blood pressure at 1:00 PM) by adding the initial blood pressure to the final blood pressure change, BP_CHANGE, obtained at 1616.

To reiterate, several estimations of the blood pressure change from an initial time window to a final time window can be obtained using different paths in time from the initial time window to a final time window. As such, a final blood pressure change can be calculated from the several estimations, which in turn increases the confidence in the final blood pressure change that is obtained. Each of the several estimations can have an associated probability of being correct. The probability of an estimation can be the weight associated to the estimation. Additionally, every intermediate blood pressure change can itself serve as a baseline.

The ML model described above is also trained using pair-wise differences between the different windows in a similar fashion that features differences between windows are used as input for predicting final blood pressure values. That is, the training data of the ML model includes all the different ways (i.e., paths) of moving from one window to another.

The training data set can be clustered into a predetermined number of clusters. Any number of clusters are possible. In an example, the training data can be partitioned into six clusters. Any clustering technique can be used. For example, k-means clustering, connectivity-based clustering, distribution-based clustering, density-based clustering, or some other clustering technique can be used. Each cluster is represented by a representative features differences and a corresponding change in blood pressure. The clusters are formed on the feature space.

The results of the clustering can be used by the function GET_PREDICTION_WEIGHTS at 1614 of FIG. 16 to obtain the weights PRED_W. Thus, while not specifically shown in equation (2), each of the $\theta_{i,j}^{k=0...K}$ can itself be calculated as a weighted sum. As is known, training a ML model can include a training phase and a testing phase. A testing data set is used to test the performance of the ML model. Based on the prediction performance (e.g., accuracy of, or confidence level in, the prediction of the change in blood pressure) on the training data set, each of the prediction values is assigned a respective weight. The weight can be the ratio of the total accurate guesses of the cluster divided by the total guesses of the cluster. In general, the weights can be set based on the training dataset. Other ways of obtaining the weight are possible. In an example, an absolute error (AE) value can be used. The absolute error can be calculated as AE=|target value−predicted value|, where target value is the value obtained from the training data set and predicted value is the value obtained from the ML model.

Clustering can be used for weight assignment. For each sample, the weights can be selected from the training data in the closest cluster. To illustrate, the training data can be split into K clusters, based on the feature values. Each cluster can have different ranges of a target (e.g., change in blood pressure). For example a first cluster (e.g., cluster 1) can have samples with ΔSBP in the range [−5, 20], and a second cluster (e.g., cluster 2) can have samples with ΔSBP in the range [−5, 25]. Thus, both clusters have samples with target values in the range [−5, 20]. This can happen for a variety of reasons. For example, with respect to blood pressure changes, the reasons can include personal differences in people. For example, two target values (e.g., change in blood pressure ΔSBP=10 mmHg samples) can be obtained from a 65-year-old person and a 25-year-old person. However, the feature values of these two samples may be significantly different from each other, even though they result in the same target value. Clustering can be used to assign an appropriate weight to a predicted value based on the feature values used to obtain the predicted value.

In each cluster, the weight of a predicted value is calculated. As such, equal predictions in two different clusters can have different weights. To illustrate, and without any loss of generality, in the first cluster, if the predicted value ΔSBP is −5, then the weight w=0.14, if the predicted value ΔSBP is −4, then the weight w=0.3, if the predicted value ΔSBP is −3, then the weight w=0.25, and so on; and in the second cluster, if the predicted value ΔSBP is −5, then the weight w=0.21, if the predicted value ΔSBP is −4, then the weight w=0.48, if the predicted value ΔSBP is −3, then the weight w=0.61, and so on. After the weights and clusters are set using the training data, a testing procedure can start. For each sample in a testing dataset, first the cluster that the sample belongs to is found. This would be the closest cluster to the sample in the feature space. The prediction is the obtained from the ML model. Based on the predicted value, the weight is selected. For example, if the test sample belongs to cluster 1 and the predicted value is −5, then the weight w=0.14.

Returning to FIG. 15, in an example, estimating the first blood pressure change between the initial time window and the final time window can include obtaining a weight for the first blood pressure change. The weight can correspond to (i.e., can be indicative of) a confidence level of the model in the first blood pressure change. As also mentioned above, the weight can be based on data used to train the model. As also mentioned above, the weight can be obtained based on a clustering of the training data.

Figure 17:
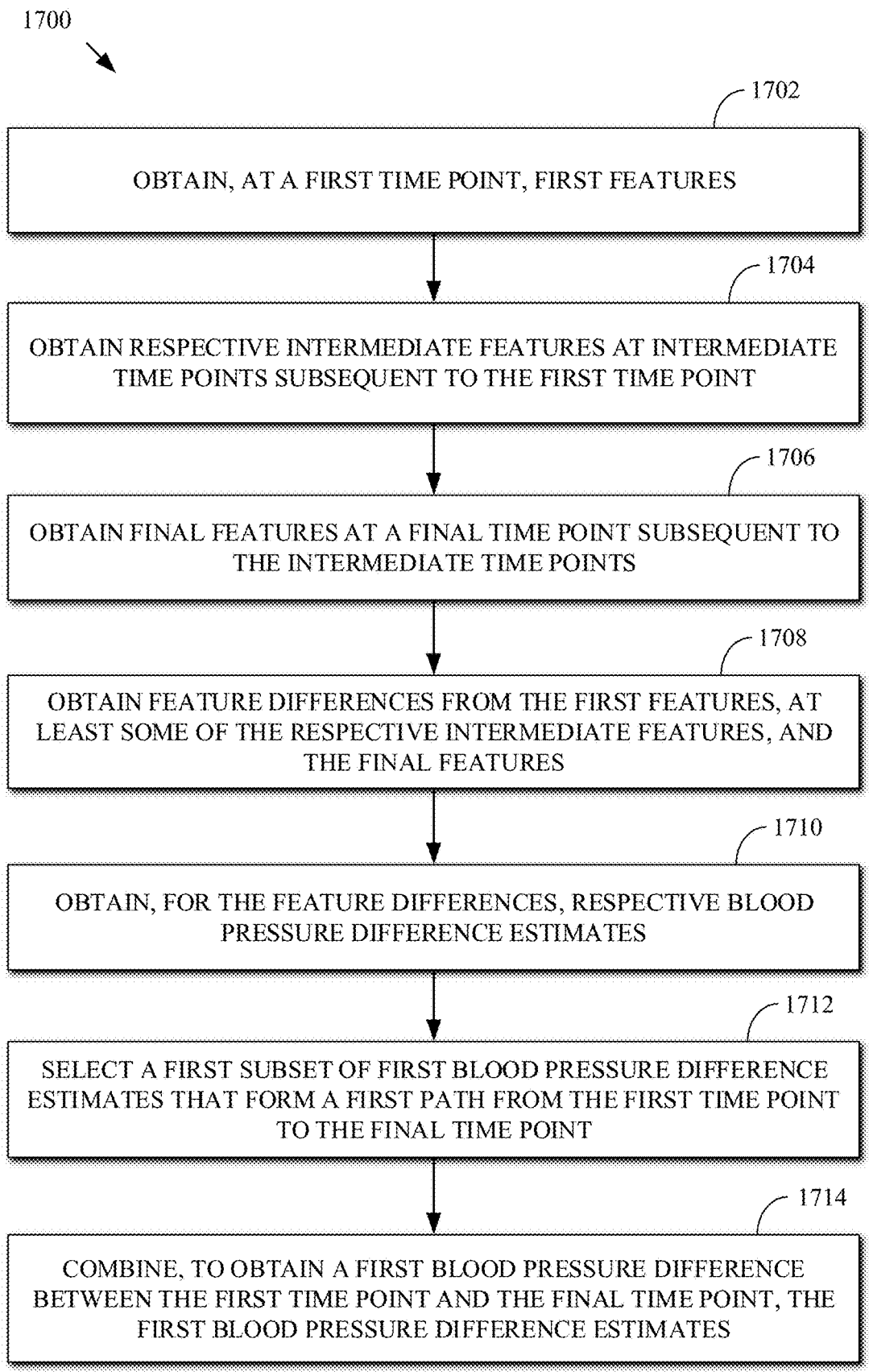
FIG. 17 is an example of another technique for estimating a blood pressure of a user according to implementations of this disclosure.

FIG. 17 is an example of another technique 1700 for estimating a blood pressure of a user according to implementations of this disclosure. The technique 1700 can be implemented by a wearable device, such as the apparatus 100 of FIG. 1 or the apparatus 900 of FIG. 9, or some other wearable device that include sensors. The sensors can include PPG sensors, a sensing module (such as the sensing module 1000 of FIG. 10, optical sensors, light sensors, pressure sensors, more sensors, fewer sensors, other sensors, or a combination thereof. The technique 1700 can be implemented, for example, as a software program that may be executed by a processor-based computing system, such as the system 800 of FIG. 8. The software program can include machine-readable instructions that may be stored in a memory such as the RAM 810 or the ROM 820 of FIG. 8, or a secondary storage, such as the storage system 830 of FIG. 8, and that, when executed by a processor, such as the processor 805, can cause the processor-based computing system to perform the technique 1700.

The technique 1700 estimates (e.g., predicts) a change in blood pressure between a first time (e.g., an initial time window) and a current time (e.g., a final time window). The technique 1700 obtains several estimates of the change in the blood pressure and combines the several estimates to obtain a final blood pressure change estimate. Each of the several estimates of the change in the blood pressure is obtained using a unique data path from the initial time window to the final time window.

The example used above with respect to FIG. 16 is used again to illustrate the technique 1700.

At 1702, the technique 1700 obtains, at a first time point, first features. Using the example used to describe FIG. 16, the first time point can be 9:00 AM. As also described above, the first features can include be features extracted from sensor data of the wearable device. At 1704, the technique 1700 obtains respective intermediate features at intermediate time points subsequent to the first time point. To illustrate, the respective intermediate features can be features obtained at 10:00 AM, 11:00, and 12:00 PM. At 1706, the technique 1700 obtains final features at a final time point subsequent to the intermediate time points. To illustrate, the final features can be obtained at 1:00 PM. The first features, the respective intermediate features, and the final features can each include sensor-based features obtained using data from sensors of a wearable device of the user. As described above, in some examples, the features can also include personal-based features relating to the user.

At 1708, the technique 1700 obtains feature differences from the first features, at least some of the respective intermediate features, and the final features. That 1700 obtains at least some pair-wise differences of the features obtained at 1702-1706. At 1710, the technique 1700 obtains, for the feature differences, respective blood pressure difference estimates.

At 1710, the technique 1700 selects, from the respective blood pressure difference estimates, a first subset of first blood pressure difference estimates that form a first path from the first time point to the final time point. To illustrate, the technique 1700 can select, as the first path, one of the paths (1 4)(4 5), (1 3)(3 4)(4 5), (1 2)(2 5), (1 2)(2 4)(4 5), (1 2)(2 3)(3 5), or (1 2)(2 3)(3 4)(4 5), which are described above. That is, the first path is one of the non-trivial paths, where the trivial path is (1 5).

At 1712, the technique 1700 can combine, to obtain a first blood pressure difference between the first time point and the final time point, the first blood pressure difference estimates of the first subset of the blood pressure difference estimates. To illustrate, the technique 1700 calculates the $\theta_{i,j}^{k}$, wherein k≠0, of equation (2) corresponding to the first path.

The technique 1700 can also include obtaining, at the first time point, a baseline blood pressure and adding the baseline blood pressure and the first blood pressure difference.

In an example, the technique 1700 can also include selecting, from the respective blood pressure difference estimates, a second subset of second blood pressure difference estimates that form a second path from the first time point to the final time point, wherein the first path is different from the second path; combining, to obtain a second blood pressure difference between the first time point and the final time point, the second blood pressure difference estimates of the second subset of the blood pressure difference estimates; and combining the first blood pressure difference and the second blood pressure difference to obtain a combined blood pressure difference. That is, the technique 1700 obtains a second estimate of the change in blood pressure.

In an example, combining the first blood pressure difference and the second blood pressure difference to obtain the combined blood pressure difference can include obtaining, based on clustering of training data, a first weight of first blood pressure difference; obtaining, based on the clustering of the training data, a second weight of first blood pressure difference; and computing the combined blood pressure difference as a weighted combination of the first blood pressure difference and the second blood pressure difference using the first weight and the second weight, respectively.

Another aspect of the disclosed implementation is a technique for predicting a final current value at a final time point in situations of imbalanced training data in machine learning. The technique can be implemented by a wearable device, such as the apparatus 100 of FIG. 1 or the apparatus 900 of FIG. 9, or some other wearable device that include sensors. The sensors can include PPG sensors, a sensing module (such as the sensing module 1000 of FIG. 10, optical sensors, light sensors, pressure sensors, more sensors, fewer sensors, other sensors, or a combination thereof. The technique can be implemented, for example, as a software program that may be executed by a processor-based computing system, such as the system 800 of FIG. 8. The software program can include machine-readable instructions that may be stored in a non-transitory computer-readable storage medium, such as the RAM 810 or the ROM 820 of FIG. 8, or a secondary storage, such as the storage system 830 of FIG. 8, and that, when executed by a processor, such as the processor 805, can cause the processor-based computing system to perform the technique.

At a first step, the technique can obtain, at an initial time point, initial predictive features, as described above. In an example, the initial time point can be used as a baseline time point. In a second step, the technique can obtain an initial measured value, as described above. In an example, the initial measured value can itself be an estimated (e.g., predicted) value. In a third step, the technique obtains intermediate predictive features at points between the initial time point and the final time point, as described above. In a fourth step, the technique obtains, at the final time point, final predictive features, as described above. In a fifth step, the technique selects a first path, as described above. The first path can correspond to a set of first data hops (e.g., time hops) from the initial time point to the final time point.

Each first data hop includes starting predictive features and ending predictive features. The starting predictive features can be one of the initial predictive features or one of the intermediate predictive features. The ending predictive features is another of the intermediate predictive features or the final predictive features. For example, if the first path is (1 4)(4 5), then in the first data hops (1 4) and (4 5), the starting predictive features are, respectively, the predictive features of $WINDOW_1$ (i.e., the "1" in (1 4)) and $WINDOW_4$ (i.e., the "4" in (4 5)); and the ending predictive features are, respectively, the predictive features of $WINDOW_4$ (i.e., the "4" in (1 4)) and $WINDOW_5$ (i.e., the "5" in (4 5)).

In a sixth step, the technique calculates first respective predictive feature differences for the first data hops, as described above. In a seventh step, the technique obtains, using the first respective predictive feature differences as inputs to a machine learning model, first respective predicted values, as described above. In an eighth step, the technique combines at least the first respective predicted values to obtain the final current value, as described above.

In an example, the predictive features can be features extracted from sensor data of a wearable device. The predictive features can be used by the machine-learning model to predict a prediction value. In an example, the prediction value can be a change in blood pressure between a first time point and a second time point. Thus, the final current value can be an estimated blood pressure.

As described above, a respective weight of an estimated current value can be based on a number of occurrences of the estimated current value in training data given the respective feature differences corresponding to the estimated current value. As also described above, the training data can be clustered to obtain the weights.

The technique can also include obtaining, using respective second predictive feature differences of second data hops of a second path as inputs to a machine learning model, second respective predicted values; and combining at least the first respective predicted values and the second respective predicted values to obtain the final current value.

For simplicity of explanation, techniques disclosed herein, including the techniques 1300, 1500, 1600, 1700 of FIGS. 13 and 15-17, are depicted and described as series of steps or operations. However, the steps or operations in accordance with this disclosure can occur in various orders and/or concurrently. Additionally, other steps or operations not presented and described herein may be used. Furthermore, not all illustrated steps or operations may be required to implement a method in accordance with the disclosed subject matter.

While implementations have been illustrated and described, it will be appreciated that various changes can be made therein without departing from the spirit and scope of the disclosure. Moreover, the various features of the implementations described herein are not mutually exclusive. Rather any feature of any implementation described herein may be incorporated into any other suitable implementation.

Additional features may also be incorporated into the described systems and methods to improve their functionality. For example, those skilled in the art will recognize that the disclosure can be practiced with a variety of physiological monitoring devices, including but not limited to heart rate and blood pressure monitors, and that various sensor components may be employed. The devices may or may not comprise one or more features to ensure they are water resistant or waterproof. Some implementations of the devices may hermetically sealed.

Other implementations of the aforementioned systems and methods will be apparent to those skilled in the art from consideration of the specification and practice of this disclosure. It is intended that the specification and the aforementioned examples and implementations be considered as illustrative only, with the true scope and spirit of the disclosure being indicated by the following claims.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise or clear from context, "X includes A or B" is intended to mean any of the natural inclusive permutations thereof. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. As used herein, the terms "determine" and "identify," or any variations thereof, include selecting, ascertaining, computing, looking up, receiving, determining, establishing, obtaining, or otherwise identifying or determining in any manner whatsoever.

Further, for simplicity of explanation, although the figures and descriptions herein may include sequences or series of operations or stages, elements of the methods disclosed herein can occur in various orders and/or concurrently. Additionally, elements of the methods disclosed herein may occur with other elements not explicitly presented and described herein. Furthermore, one or more elements of the methods described herein may be omitted from implementations of methods in accordance with the disclosed subject matter.

All of a portion of the implementations can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

All or a portion of implementations can take the form of a computer program product accessible from, for example, a tangible computer-usable or computer-readable medium. A computer-usable or computer-readable medium can be any device that can, for example, tangibly contain, store, communicate, or transport the program for use by or in connection with any processor. The medium can be, for example, an electronic, magnetic, optical, electromagnetic, or semiconductor device. Other suitable mediums are also available.

The above-described implementations have been described in order to allow easy understanding of the application and are not limiting. On the contrary, the application covers various modifications and equivalent arrangements included within the scope of the appended claims, which scope is to be accorded the broadest interpretation as is permitted under the law so as to encompass all such modifications and equivalent arrangements While the disclosure has been described in connection with certain implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A wearable device for estimating a blood pressure of a user, comprising:
   one or more sensors configured to measure characteristics related to the blood pressure of the user;
   a memory; and
   a processor, the processor configured to execute instructions stored in the memory to:
   receive the first sensor data from the one or more sensors;
   process the first sensor data to obtain, for a first time point, first features;
   receive second sensor data from the one or more sensors;
   obtain respective intermediate features at intermediate time points subsequent to the first time point by processing the second sensor data;
   obtain final features at a final time point subsequent to the intermediate time points;
   obtain feature differences from the first features, at least some of the respective intermediate features, and the final features;
   obtain, for the feature differences, respective blood pressure difference estimates;
   select, from the respective blood pressure difference estimates, a first subset of first blood pressure difference estimates that form a first path from the first time point to the final time point;
   combine, to obtain a first blood pressure difference between the first time point and the final time point, the first blood pressure difference estimates of the first subset of the first blood pressure difference estimates; and
   determine a blood pressure of the user for the final time point based on the first blood pressure difference between the first time point and the final time point.

2. The wearable device of claim 1, wherein the instructions further comprise instructions to:
   obtain, for the first time point, a baseline blood pressure, wherein the instructions to determine the blood pressure of the user for the final time point based on the first blood pressure difference further comprise instructions to determine the blood pressure of the user for the final time point by adding the baseline blood pressure and the first blood pressure difference.

3. The wearable device of claim 1, wherein the first features, the respective intermediate features, and the final features each includes sensor-based features obtained using data from sensors of a wearable device of the user.

4. The wearable device of claim 3, wherein the sensor-based features obtained using the data from the sensors include at least one pulse transit time, an amount of pressure that blood exerts on a skin surface of the user, or a pulse front velocity.

5. The wearable device of claim 1, wherein the first features, the respective intermediate features, and the final features each further includes personal-based features relating to the user.

6. The wearable device of claim 1, wherein the instructions further comprise instructions to:
   select, from the respective blood pressure difference estimates, a second subset of second blood pressure difference estimates that form a second path from the first time point to the final time point, wherein the first path is different from the second path;
   combine, to obtain a second blood pressure difference between the first time point and the final time point, the second blood pressure difference estimates of the second subset of the blood pressure difference estimates; and
   combine the first blood pressure difference and the second blood pressure difference to obtain a combined blood pressure difference.

7. The wearable device of claim 6, wherein the instructions to determine the blood pressure of the user for the final time point based on the first blood pressure difference further comprise instructions to:
   add a baseline blood pressure and the combined blood pressure difference to obtain the blood pressure of the user for the final time point.

8. The wearable device of claim 6, wherein to combine the first blood pressure difference and the second blood pressure difference to obtain the combined blood pressure difference, comprises to:
   obtain, based on clustering of training data, a first weight of first blood pressure difference;
   obtain, based on the clustering of the training data, a second weight of first blood pressure difference; and
   compute the combined blood pressure difference as a weighted combination of the first blood pressure difference and the second blood pressure difference using the first weight and the second weight, respectively.

9. The wearable device of claim 1, wherein the first subset of first blood pressure difference estimates comprises a first blood pressure difference estimate from the first time point to an intermediate time point and a first blood pressure difference estimate from the intermediate time point to the final time point; and
   wherein to combine the first blood pressure difference estimates of the first subset of the blood pressure difference estimates, comprises:
   adding, to obtain the first blood pressure difference from the first time point to the final time point, the first blood pressure difference estimate from the first time point to an intermediate time point and the first blood pressure difference estimate from the intermediate time point to the final time point.

10. A non-transitory computer-readable storage medium, comprising executable instructions that, when executed by a processor, facilitate performance of operations for predicting a final current value at a final time point in situations of imbalanced training data in machine learning, the operations comprising:

receiving first sensor data from sensors of a wearable device, wherein the sensors of the wearable device are configured to measure characteristics related to a blood pressure of a user associated with the wearable device;

processing the first sensor data to obtain, at an initial time point, initial predictive features;

obtaining, at the initial time point, an initial measured value;

receiving second sensor data from the sensors of the wearable device;

processing the second sensor data to obtain intermediate predictive features at points between the initial time point and the final time point;

obtaining, at the final time point, final predictive features;

selecting a first path,
- wherein the first path corresponds to a set of first data hops from the initial time point to the final time point,
- wherein each first data hop includes starting predictive features and ending predictive features,
- wherein the starting predictive features is one of the initial predictive features or one of the intermediate predictive features, and
- wherein the ending predictive features is another of the intermediate predictive features or the final predictive features;

calculating first respective predictive feature differences for the first data hops;

obtaining, using the first respective predictive feature differences as inputs to a machine learning model, first respective predicted values; and determining, by combining at least the first respective predicted values to obtain an estimated blood pressure of the user associated with the wearable device.

11. The non-transitory computer-readable storage medium of claim 10, wherein a respective weight of an estimated current value is based on a number of occurrences of the estimated current value in training data given the respective feature differences corresponding to the estimated current value.

12. The non-transitory computer-readable storage medium of claim 11, wherein the training data is clustered using to obtain the respective weight.

13. The non-transitory computer-readable storage medium of claim 11, wherein the operations further comprising:
- obtaining, using respective second predictive feature differences of second data hops of a second path as inputs to a machine learning model, second respective predicted values; and
- combining at least the first respective predicted values and the second respective predicted values to obtain the estimated blood pressure of the user associated with the wearable device.

14. A method for estimating a blood pressure of a user using a wearable device, comprising:
receiving first sensor data from one or more sensors associated with the wearable device processing the first sensor data to obtain, for a first time point, first features;

receiving second sensor data from the one or more sensors;

configured to measure characteristics related to the blood pressure of the user;

obtaining respective intermediate features at intermediate time points subsequent to the first time point by processing the second sensor data;

obtaining final features at a final time point subsequent to the intermediate time points;

obtaining feature differences from the first features, at least some of the respective intermediate features, and the final features;

obtaining, for the feature differences, respective blood pressure difference estimates;

selecting, from the respective blood pressure difference estimates, a first subset of first blood pressure difference estimates that form a first path from the first time point to the final time point;

combining, to obtain a first blood pressure difference between the first time point and the final time point, the first blood pressure difference estimates of the first subset of the blood pressure difference estimates; and determining a blood pressure of the user for the final time point based on the first blood pressure difference between the first time point and the final time point.

15. The method of claim 14, wherein the first features, the respective intermediate features, and the final features each further includes personal-based features relating to the user.

16. The method of claim 14, further comprising:
selecting, from the respective blood pressure difference estimates, a second subset of second blood pressure difference estimates that form a second path from the first time point to the final time point, wherein the first path is different from the second path;

combining, to obtain a second blood pressure difference between the first time point and the final time point, the second blood pressure difference estimates of the second subset of the blood pressure difference estimates; and combining the first blood pressure difference and the second blood pressure difference to obtain a combined blood pressure difference;

wherein determining the blood pressure of the user for the final time point based on the first blood pressure difference further comprises adding a baseline blood pressure and the combined blood pressure difference to obtain the blood pressure of the user for the final time point.

17. The method of claim 16, wherein combining the first blood pressure difference and the second blood pressure difference to obtain the combined blood pressure difference, comprises:
obtaining, based on clustering of training data, a first weight of first blood pressure difference;

obtaining, based on the clustering of the training data, a second weight of first blood pressure difference; and computing the combined blood pressure difference as a weighted combination of the first blood pressure difference and the second blood pressure difference using the first weight and the second weight, respectively.

18. The method of claim 14, wherein the first features include at least one of a pulse transit time, an amount of pressure that blood exerts on a skin surface of the user, or a pulse front velocity.

19. The method of claim 14, further comprising:
obtaining a baseline blood pressure for the first time point; and wherein determining the blood pressure of the user for the final time point based on the first blood pressure difference further comprises:
obtaining the blood pressure of the user for the final time point by adding the baseline blood pressure and the first blood pressure difference.

* * * * *